(12) United States Patent
Reid

(10) Patent No.: US 9,390,228 B2
(45) Date of Patent: Jul. 12, 2016

(54) SYSTEM AND METHOD FOR SECURELY STORING AND SHARING INFORMATION

(71) Applicant: REID CONSULTING GROUP, Athens, OH (US)

(72) Inventor: Thomas Alan Reid, Athens, OH (US)

(73) Assignee: Reid Consulting Group, Inc., Athens, OH (US)

( * ) Notice: Subject to any disclaimer, the term of this patent is extended or adjusted under 35 U.S.C. 154(b) by 14 days.

(21) Appl. No.: 14/539,614

(22) Filed: Nov. 12, 2014

(65) Prior Publication Data

US 2015/0074409 A1 Mar. 12, 2015

Related U.S. Application Data

(63) Continuation-in-part of application No. 13/665,861, filed on Oct. 31, 2012.

(60) Provisional application No. 61/553,883, filed on Oct. 31, 2011.

(51) Int. Cl.
*H04L 29/06* (2006.01)
*G06F 19/00* (2011.01)
*G06F 21/62* (2013.01)

(52) U.S. Cl.
CPC .......... *G06F 19/322* (2013.01); *G06F 21/6218* (2013.01); *H04L 63/0428* (2013.01); *H04L 63/0435* (2013.01); *H04L 63/061* (2013.01)

(58) Field of Classification Search
CPC ... G06F 19/322; G06F 19/324; G06F 19/327; G06F 21/6218; G06F 21/60; G06F 17/30233; H04L 63/0815; H04L 63/0435
See application file for complete search history.

(56) References Cited

U.S. PATENT DOCUMENTS

| | | |
|---|---|---|
| 2008/0104705 A1 | 5/2008 | Hasbun |
| 2009/0228950 A1 | 9/2009 | Reed et al. |
| 2010/0122120 A1 | 5/2010 | Lin |
| 2011/0055202 A1 | 3/2011 | Heimendinger |

(Continued)

OTHER PUBLICATIONS

International Search Report and Written Opinion dated Feb. 2, 2016; International Application No. PCT/US2015/059717; International File Date Nov. 9, 2015.

*Primary Examiner* — Yin-Chen Shaw
*Assistant Examiner* — Arya Golriz
(74) *Attorney, Agent, or Firm* — Vorys, Sater, Seymour and Pease LLP

(57) ABSTRACT

A method for any community of interest to conduct secure exchange of encrypted data using a three-party security mechanism consisting of key masters, registries and cloud lockboxes. The registries establish unique identities, verify authenticity, and create directories of individuals, members, cloud lockboxes and other registries. The registries manage permissions lists communicated to the cloud lockboxes as well as detecting and halting anomalous activity. The key masters operated by members to manage keys for individuals, handle encryption and decryption and conduct key exchanges with other members. The cloud lockboxes manage file storage, retrieval and access control. Related application programming interfaces support multiple levels of integration and generate metadata specific to the needs of the community of interest. Community of interest establishes operating parameters including: selecting an encryption algorithm, establishing identity verification processes and selecting a security level. The design supports several other key features.

32 Claims, 18 Drawing Sheets

(56) References Cited

U.S. PATENT DOCUMENTS

| | | |
|---|---|---|
| 2011/0066863 A1 | 3/2011 | Katzenbeisser et al. |
| 2012/0257759 A1 | 10/2012 | Nick et al. |
| 2013/0275470 A1 | 10/2013 | Cao et al. |
| 2013/0297662 A1* | 11/2013 | Sharma ............... H04L 63/0815 707/827 |
| 2014/0046708 A1 | 2/2014 | Werner |
| 2014/0068202 A1 | 3/2014 | Goddard |
| 2014/0082749 A1* | 3/2014 | Holland ................ G06F 21/645 726/29 |
| 2014/0129047 A1* | 5/2014 | Barrett ..................... G07C 5/00 701/1 |
| 2014/0245012 A1 | 8/2014 | Arya et al. |

\* cited by examiner

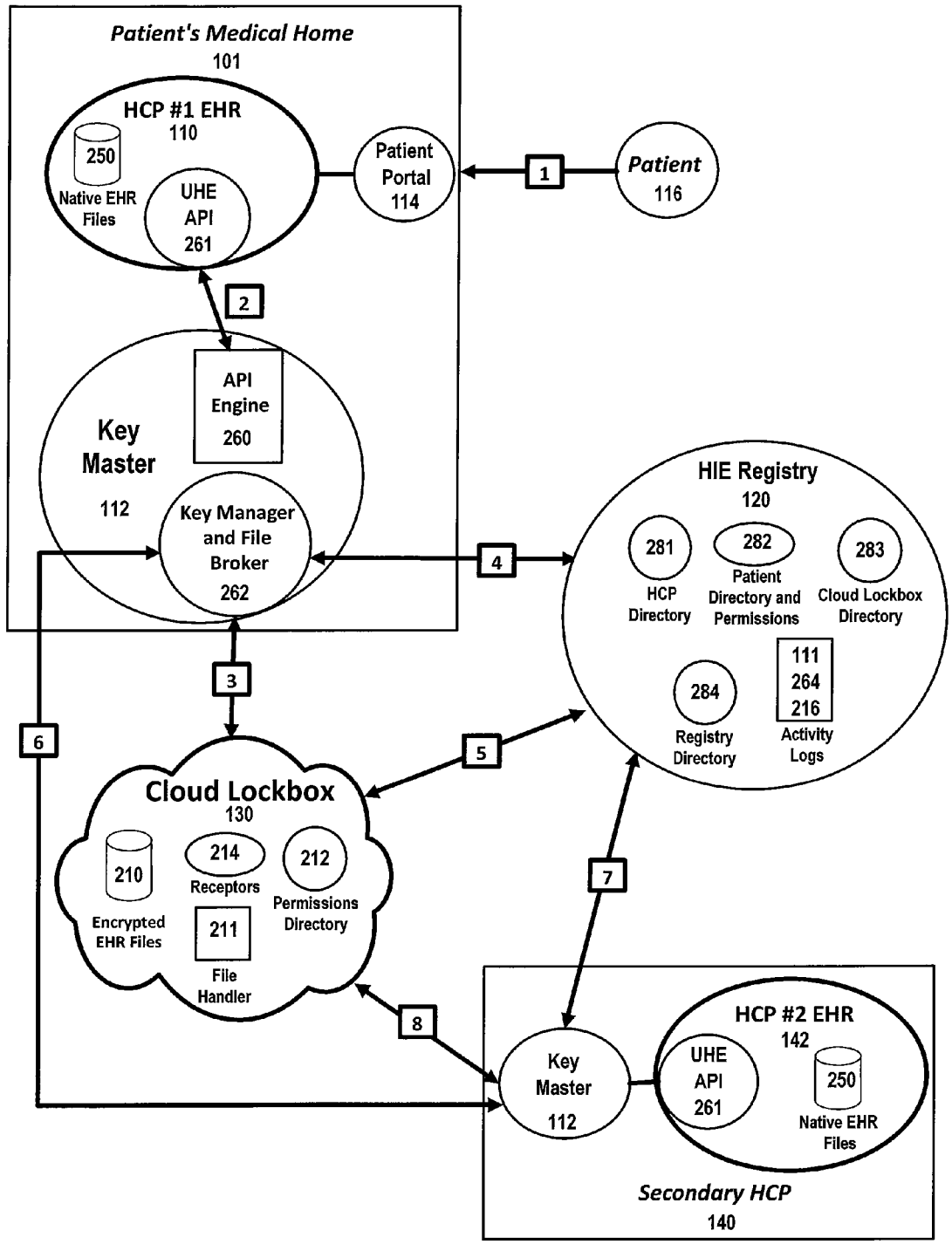
Figure 2: UHE in Action

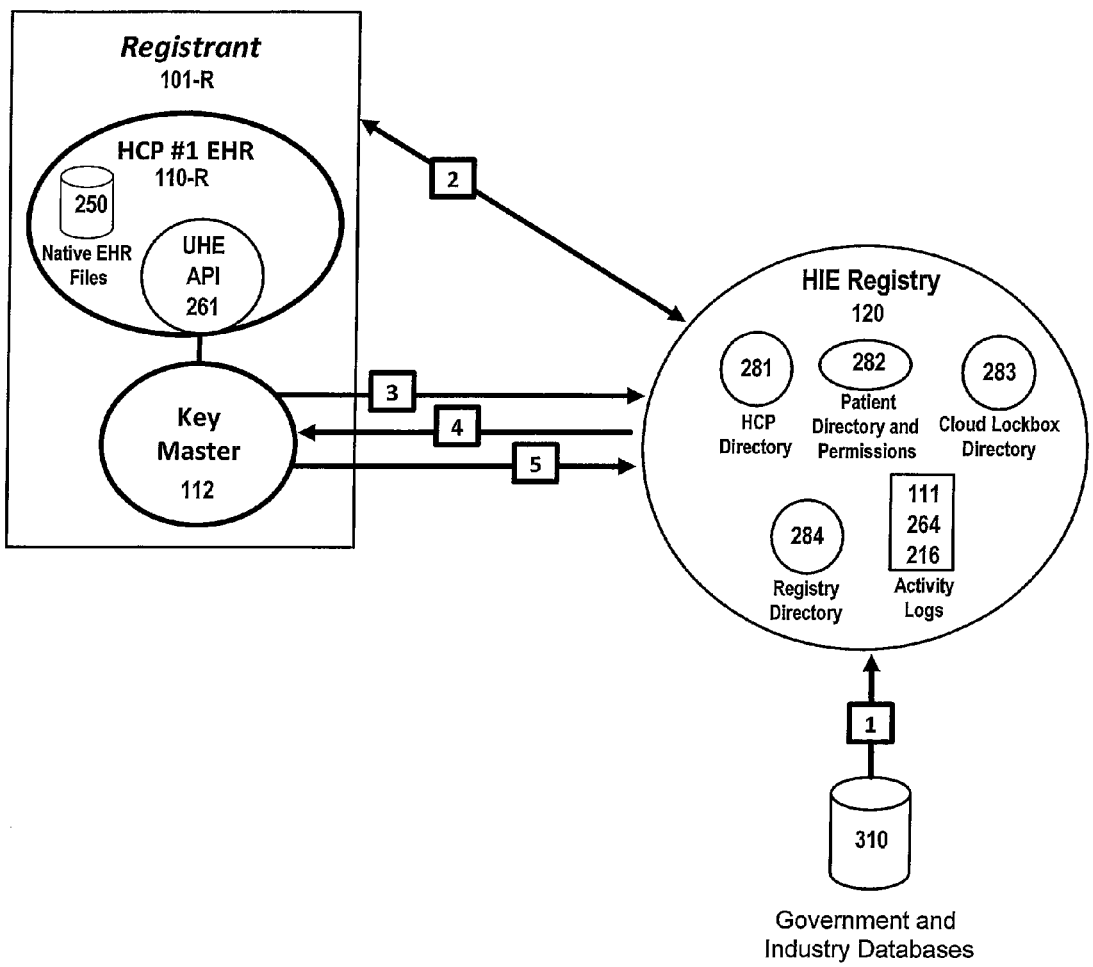
Figure 3: HCP Registration

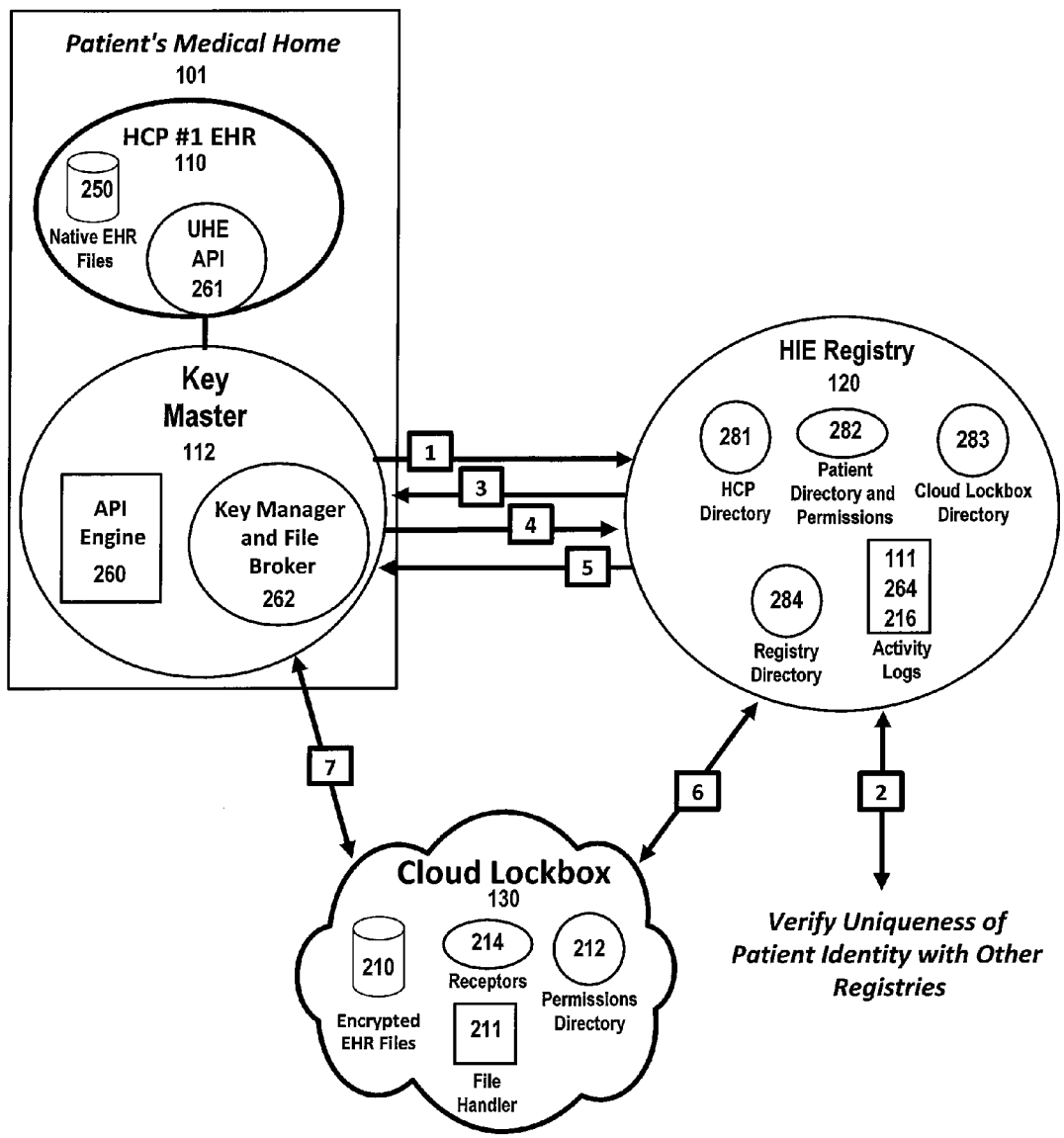
Figure 4: Registration of a Patient

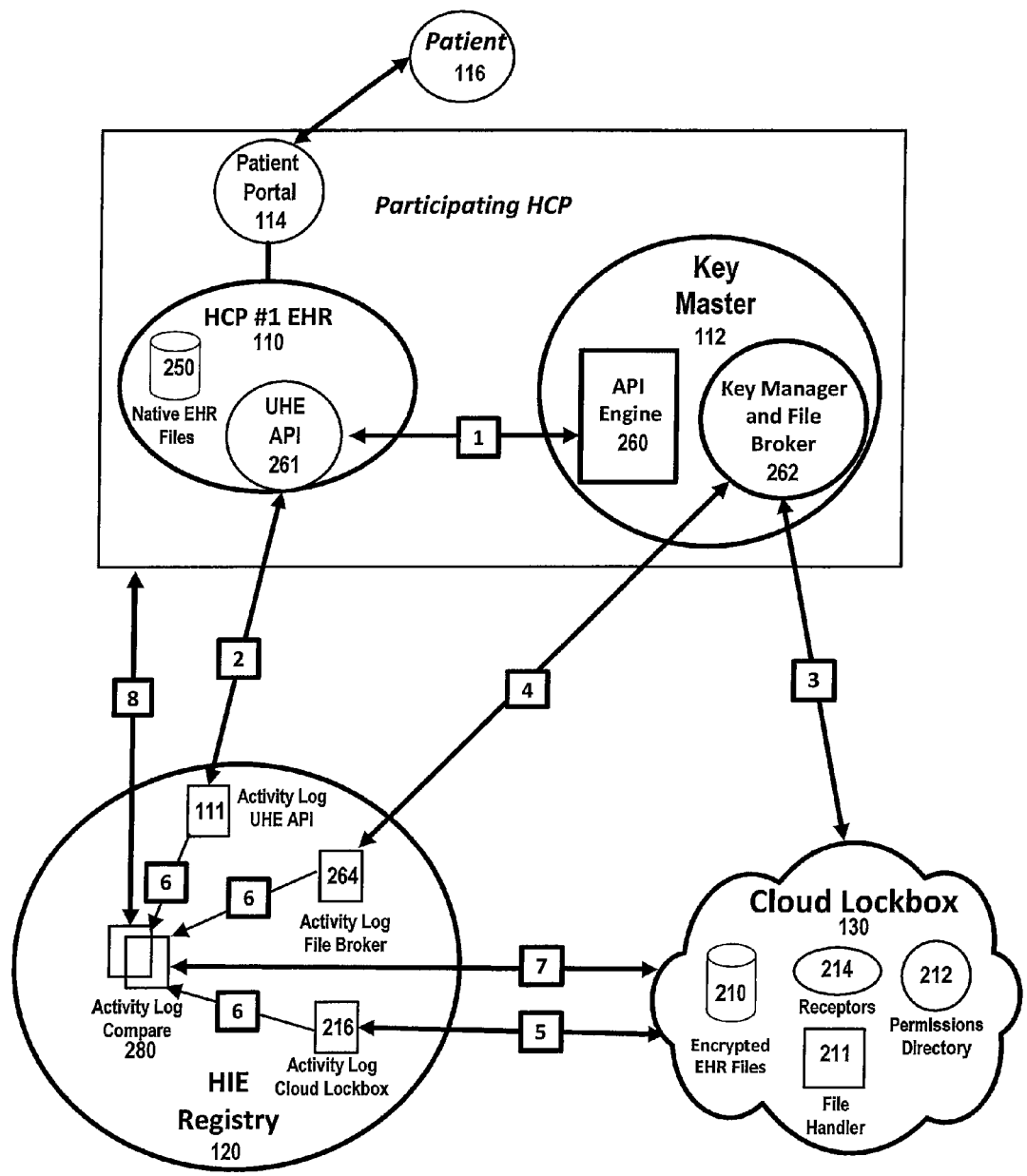
Figure 5: Activity Logs

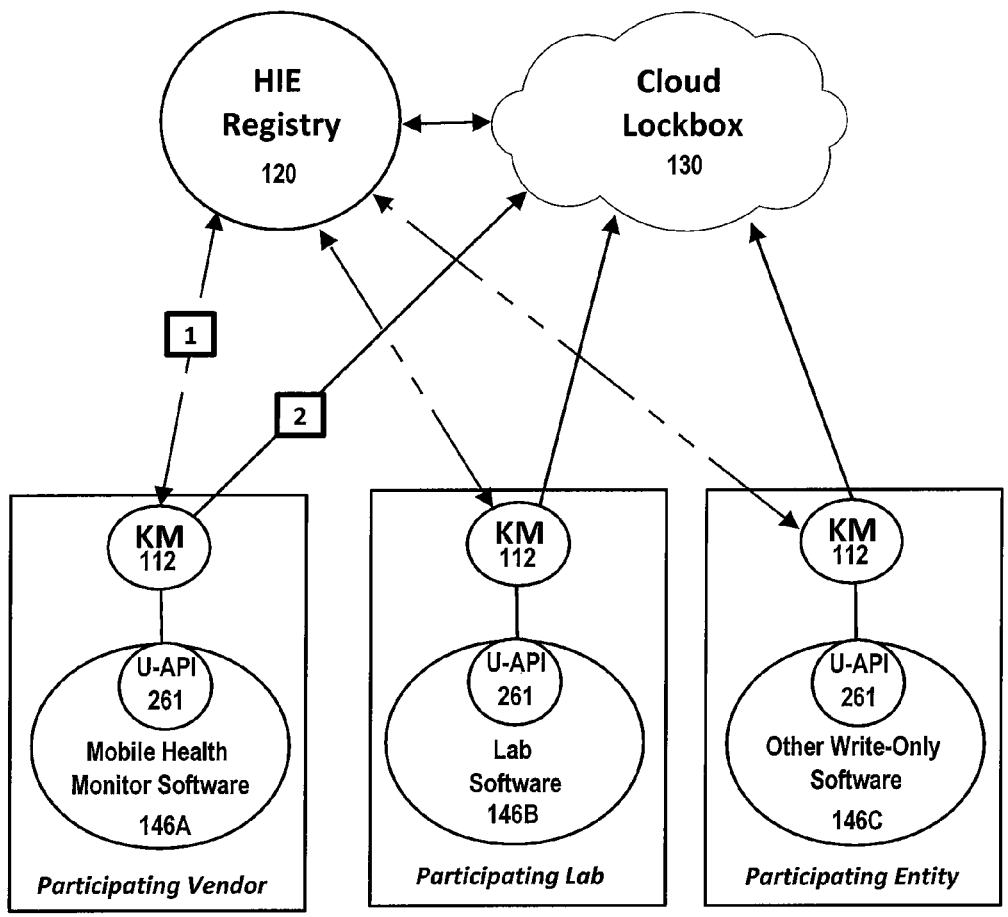
Figure 6: Write Only Members

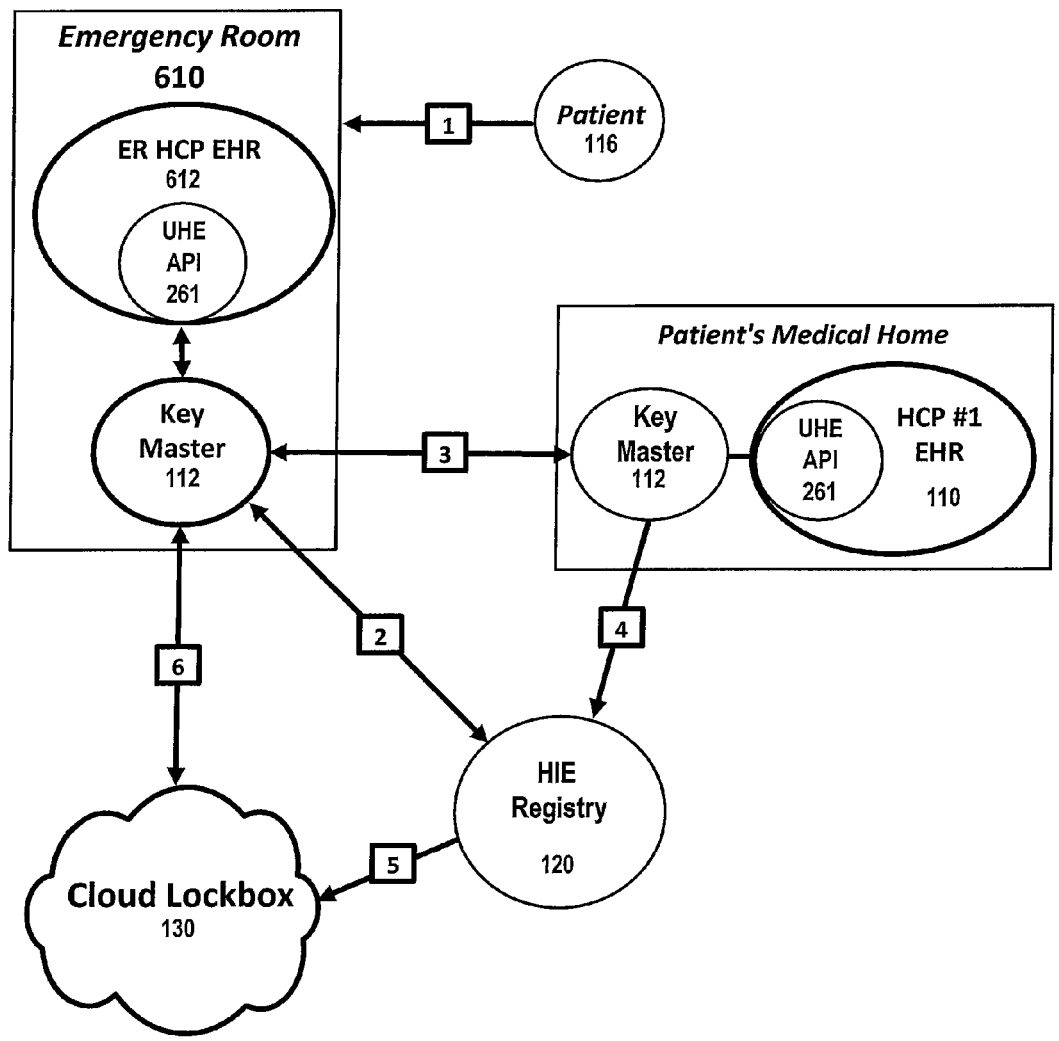
Figure 7: "Glass Break" Scenario

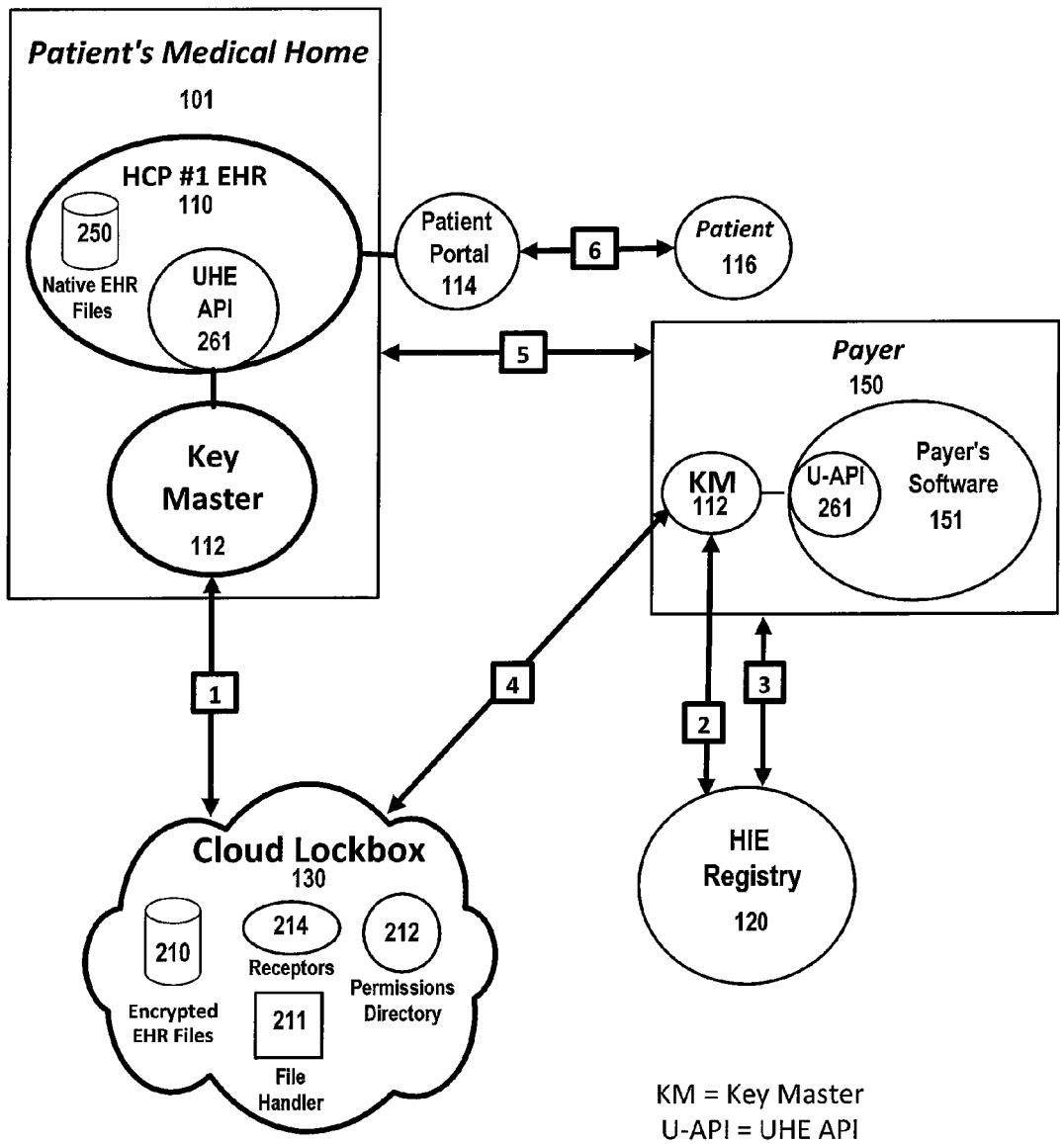
Figure 8 : Waste Fraud and Abuse Prevention

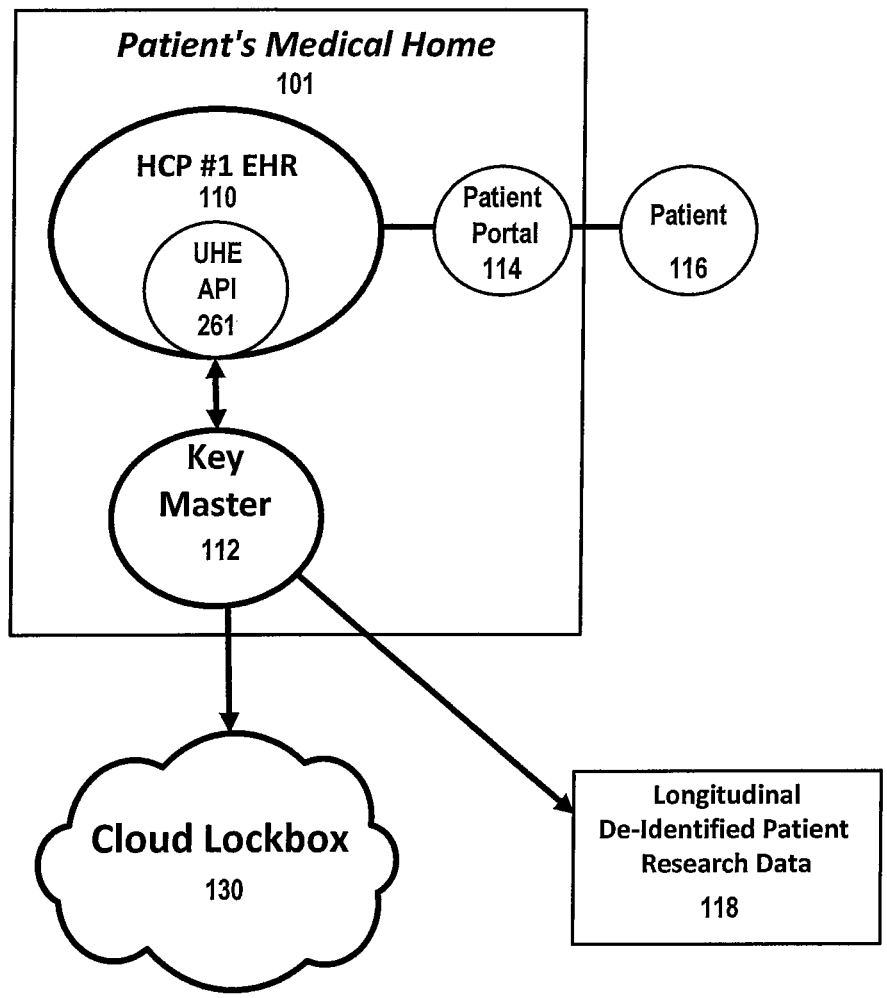
Figure 9: Support for Medical Research

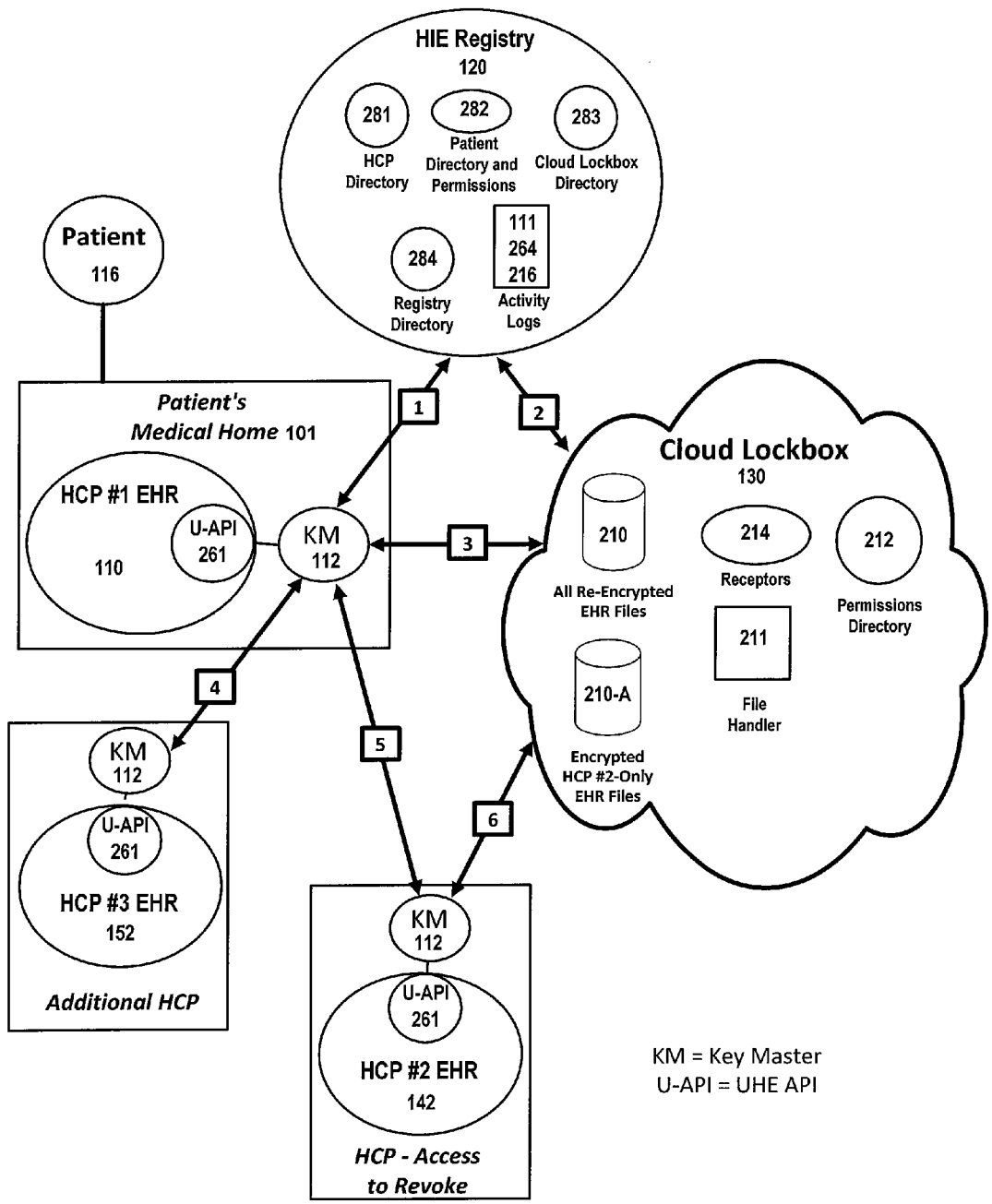
Figure 10: Key Change and/or Revoking Access

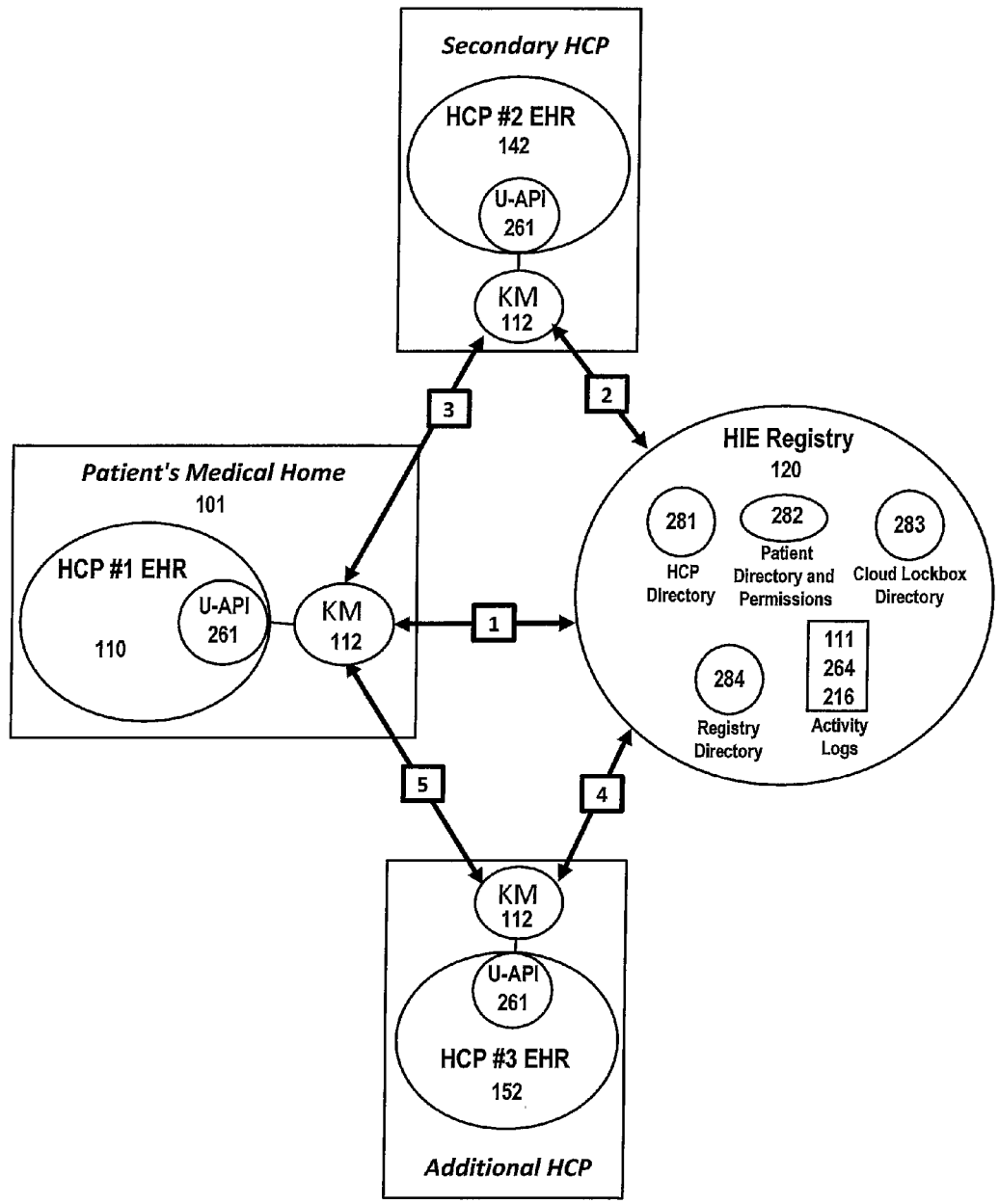
Figure 11: Key Recovery Processes

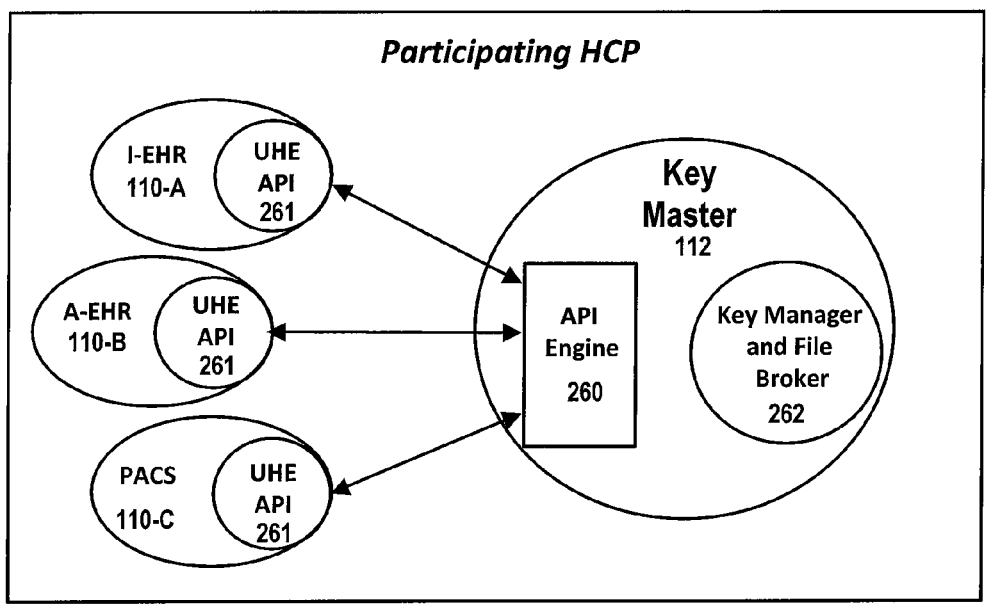
Figure 12: Multiple Software EHRs to a Single Key Master

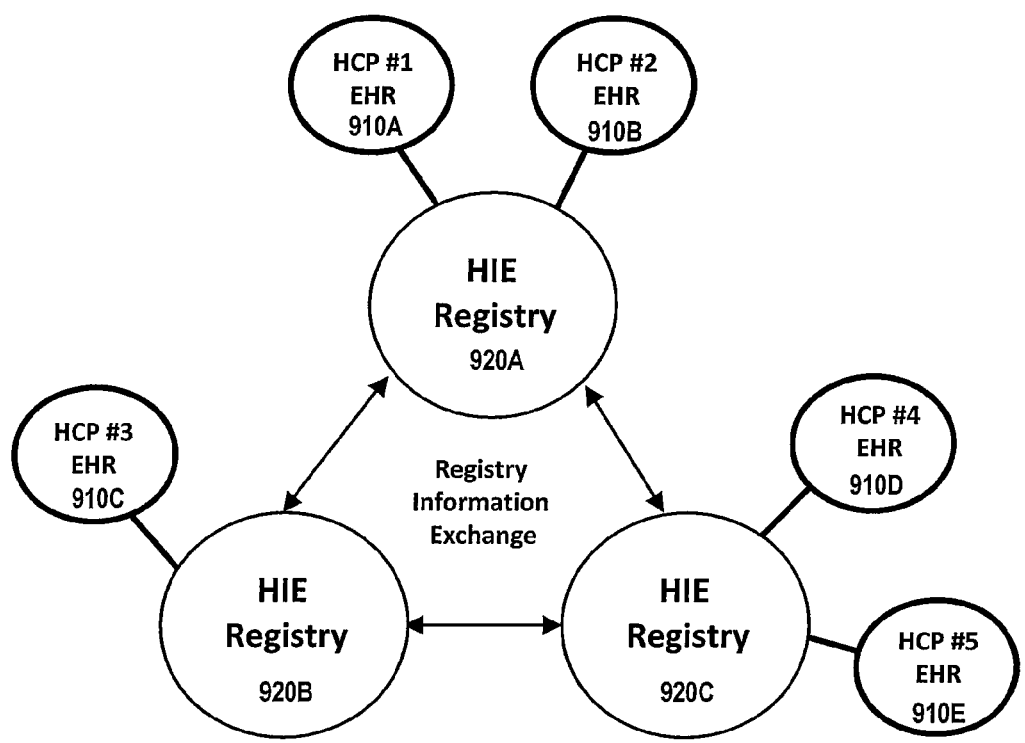
Figure 13: Registry-to-Registry Communications

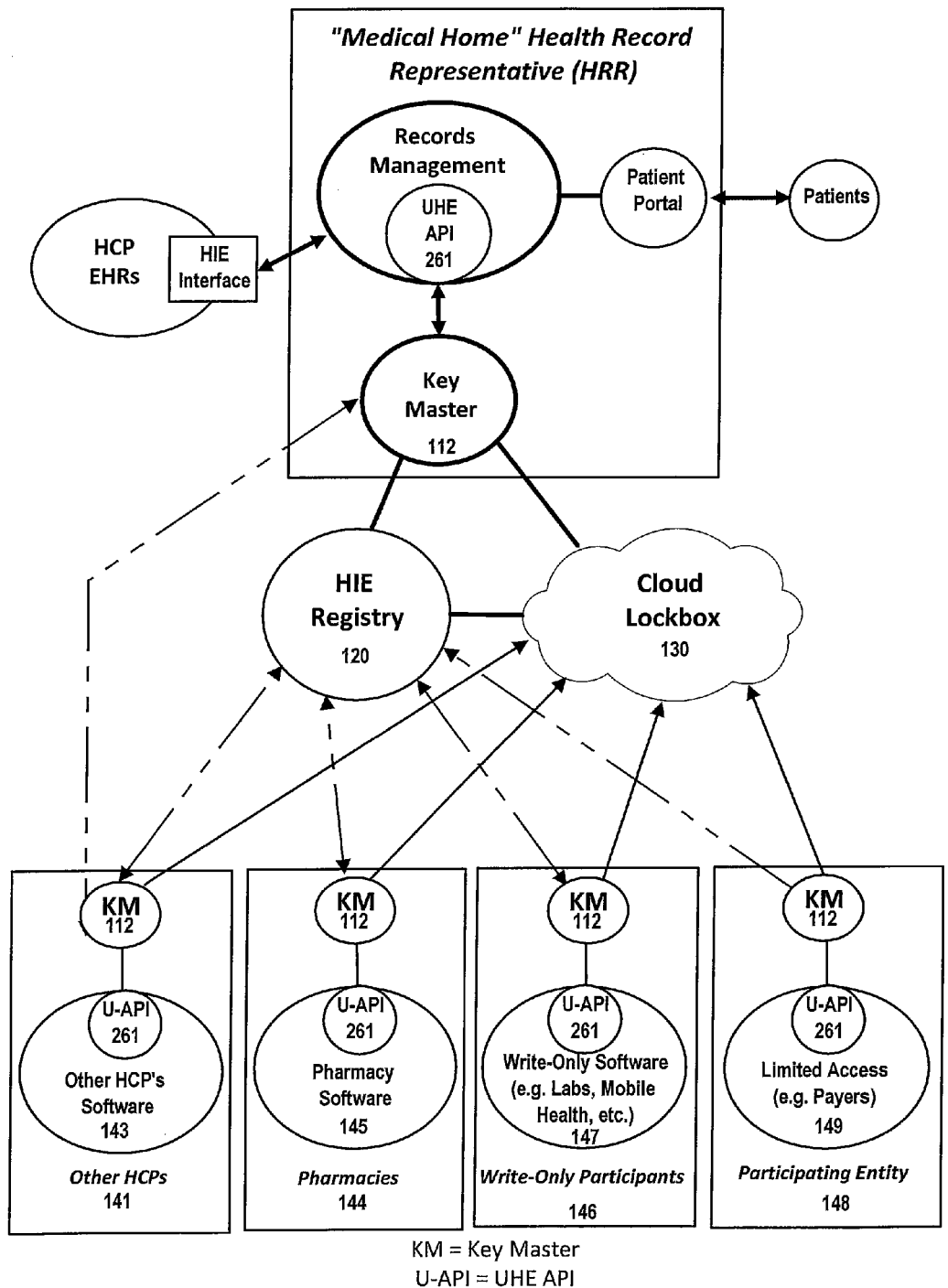
Figure 15: Health Record Representative Model

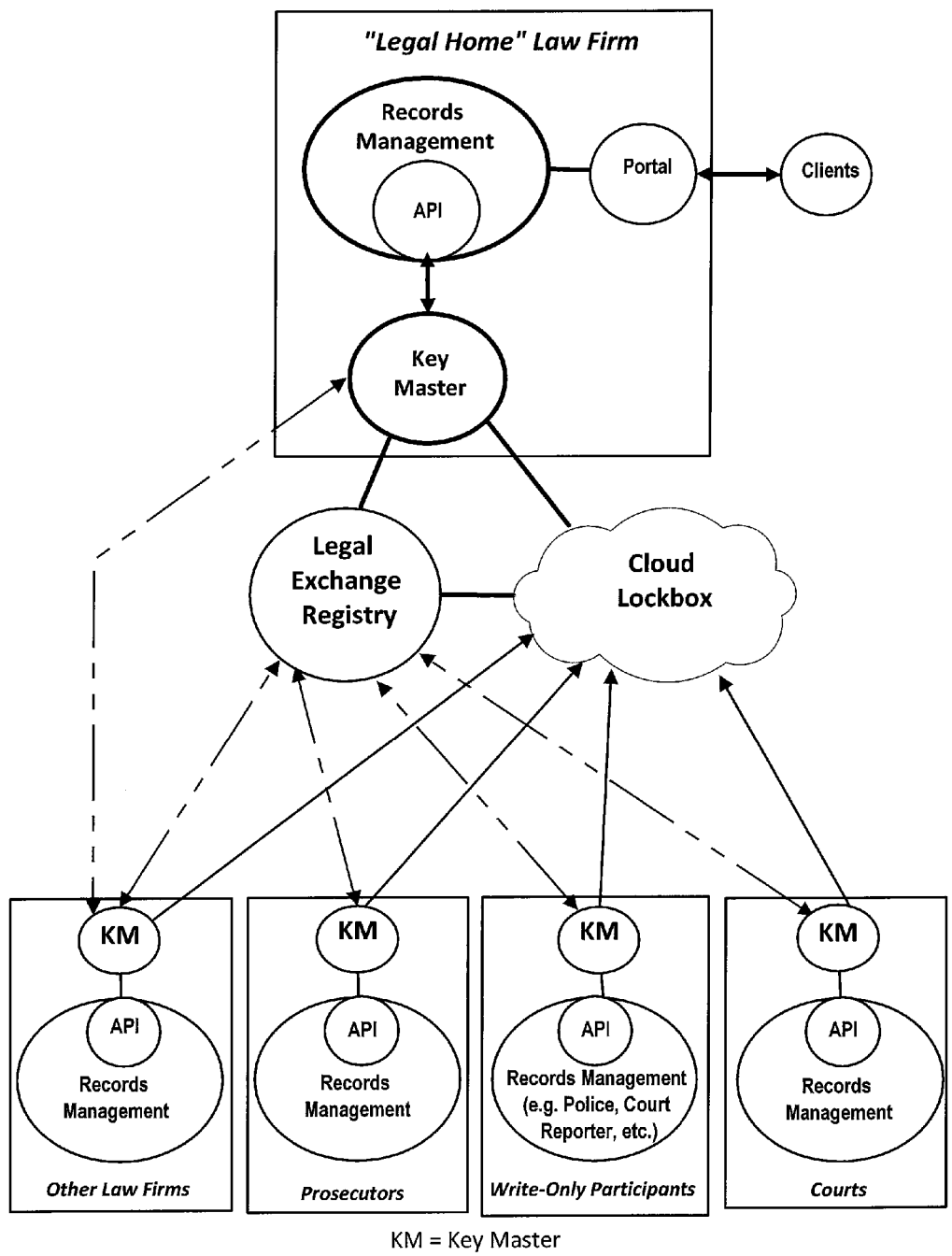
Figure 16: Legal Industry Model

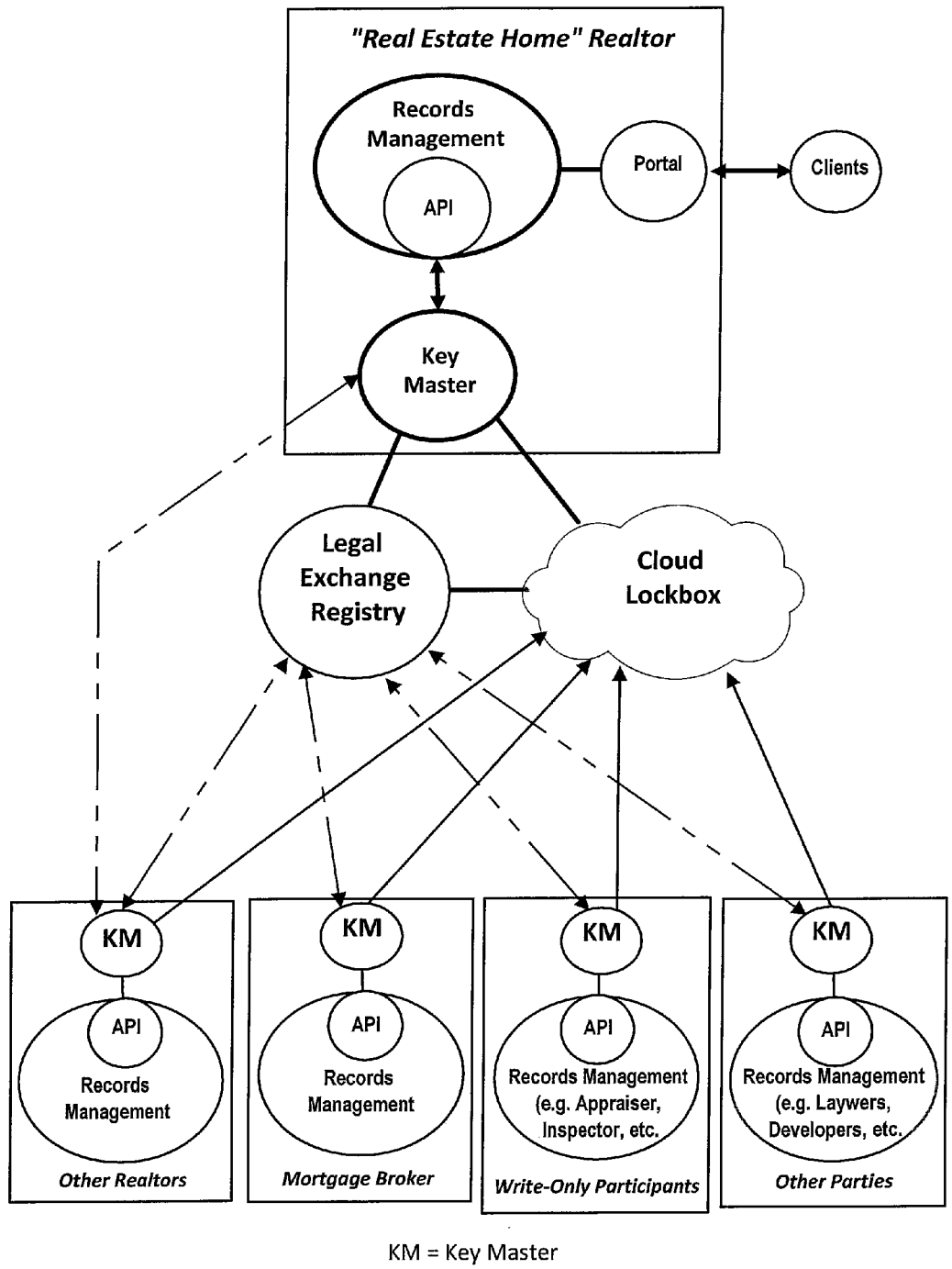
Figure 17: Real Estate Industry Model

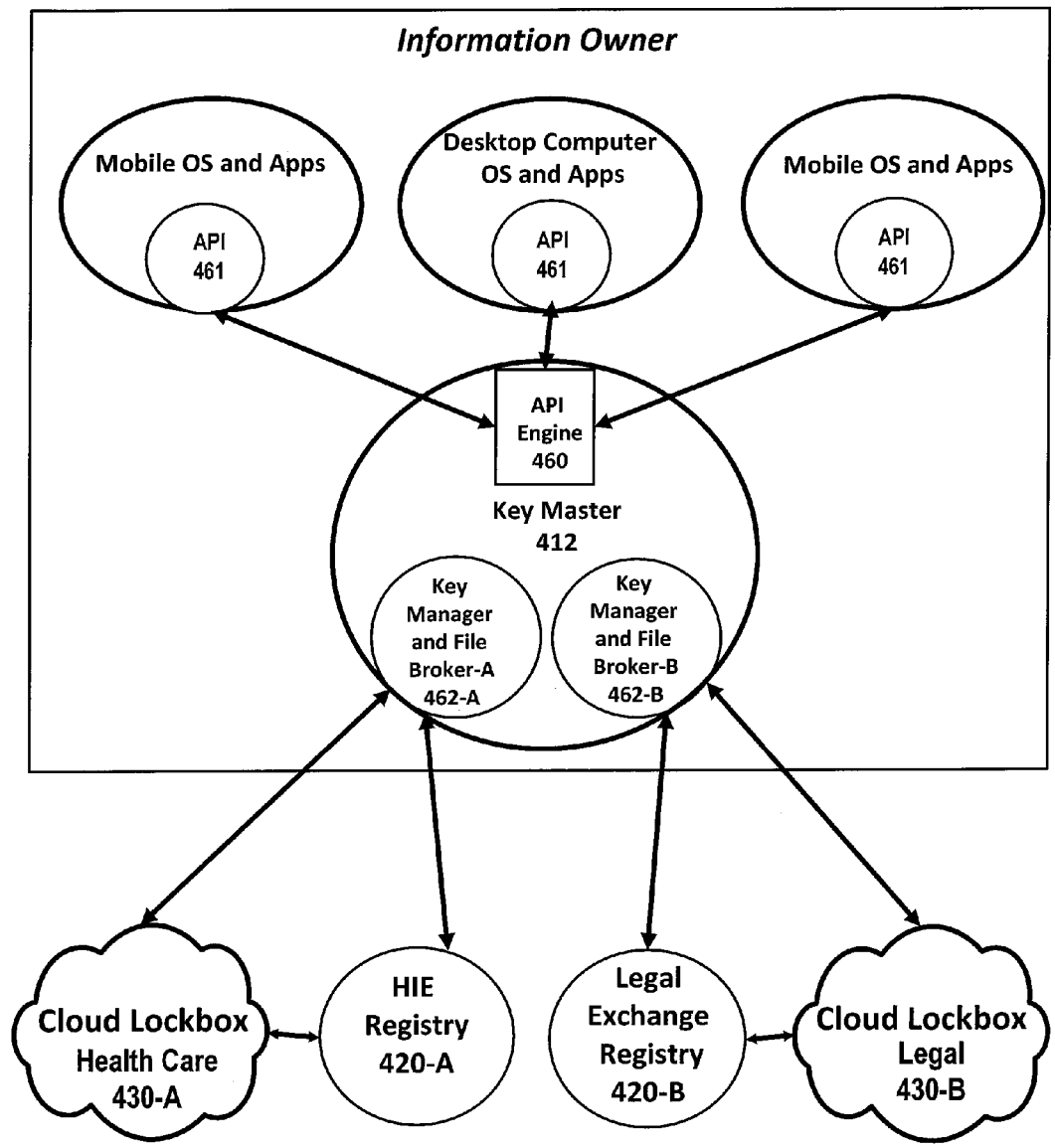
Figure 18: Information Owner Hosted and Multiple Encryption Algorithms

SYSTEM AND METHOD FOR SECURELY STORING AND SHARING INFORMATION

CROSS-REFERENCE TO RELATED APPLICATIONS

This application is a continuation-in-part of U.S. application Ser. No. 13/665,861 filed on Oct. 31, 2012, which claims priority to U.S. Provisional Patent Application Ser. No. 61/553,883 entitled "System and Method for Securely Storing and Sharing Information" filed Oct. 31, 2011, both of which are incorporated by reference in its entirety as if fully set forth herein.

TECHNICAL FIELD

The present application generally relates to systems, devices, and methods to conduct the secure exchange of encrypted data using a three-party security mechanism consisting of the members, the registries, and the cloud lockboxes. Control of the private key required for decryption is maintained by the information owner. More specifically, the mechanism establishes unique identities, verifies authenticity, generates and securely exchanges encryption key pairs, encrypts, transmits, receives and decrypts data to/from cloud lockboxes; creates and appends metadata specific to the applications and retrieves and/or acts upon metadata. The related application programming interfaces support multiple levels of integration and generate metadata specific to the needs of the application. A community of interest establishes operating parameters including: selecting an encryption algorithm, establishing identity verification processes, and selecting a security level. The design supports several other key features using operating protocols and/or metadata.

BACKGROUND

Certain methods and systems have previously been used for securely storing and sharing confidential information. Some such systems employ cryptography, such as public/private key encryption, to protect information and/or identity management.

Cryptography can provide strong protection, but the key exchange process makes sharing encrypted data clumsy and sometimes insecure. Weak, absent, or disconnected identity verification also degrades the effectiveness.

Accordingly, there is a need for systems, methods, and devices that enable secure exchange of encryption keys among any community of interest. Specifically, a need exists for a system for securely storing and sharing information which manages encryption keys separately from the encrypted information to limit access to underlying information only to those who are authorized and that integrated identity management and verification as part of the process.

SUMMARY

According to a first aspect of the present application, a method to conduct secure exchange of encrypted data using a three-party security mechanism consisting of the key masters operated by the members of the community of interest, the registries, and the cloud lockboxes. The registries establish unique identities, verify authenticity, and create directories of individuals, members, organizations, key masters, cloud lockboxes and other registries. The registries manage permissions lists communicated to the cloud lockboxes, as well as detecting and halting anomalous activity. The members operate key master software, preferably provisioned as an appliance, to create and manage keys for individuals, handle encryption, and decryption and conduct key exchanges with other members. The cloud lockboxes manage file storage, retrieval, and access control. The related application programming interfaces support with multiple levels of integration and generate metadata specific to the needs of the application. A community of interest establishes operating parameters including: selecting an encryption algorithm, establishing identity verification processes, and selecting a security level.

According to the second aspect of the present application, a method for creating a community of interest is disclosed. Any community of interest can establish its own operating parameters including: selecting a public key encryption algorithm, selecting a registry or registries, establishing related membership requirements and identity verification processes, selecting a cloud storage provider or providers, selecting the optional security features, and determining the minimum application integration levels.

According to the third aspect of the present application, a method for creating features through protocols operating among the parties and metadata is disclosed. The protocols and metadata enable features including: detection and halting of anomalous access, time-to-live settings on the sharing of data; key change and access revocation processes; key and file recovery processes, de-identification of data to feed research databases, and emergency access protocols. The design supports addition of features by leveraging existing design elements and expanding operating protocols and metadata.

According to the fourth aspect of the present application, a method for minimizing the exposure of data to system administrators is disclosed. The protected data is encrypted prior to reaching the cloud lockbox, the cloud lockbox never has the decryption key, thus the system administrator performing duties for performance optimization and maintenance of the cloud lockboxes has access to the encrypted data but does not have the decryption key. Further, when application owners elect to integrate the present application into their native data storage solutions, the benefits of this aspect extend into the premises-based or cloud-based storage of the application itself.

According to the fifth aspect of the present application, a method for integrating with applications and creation of hybrid cloud and on-premises data storage solutions is disclosed. The invention provides robust approaches for the integration of an application into the community of interest by providing both published and unpublished application programming interfaces supporting multiple levels of application integration ranging from native integration to the use of industry-standard interfaces to simple archiving solutions. The method facilitates the creation of hybrid cloud and on-premises storage solutions with predictive caching; and provides a method to integrate disparate applications within a single enterprise or across multiple enterprises.

According to the sixth aspect of the present application, a method for offering a variety of security levels is disclosed. The invention can be deployed in various ways to achieve the security level desired by the community of interest ranging from:

a. the stringent Federal Information Processing Standards 140-2 Level 4;
b. rigorous civilian standards for protecting confidentiality such as Health Information Portability and Accountability Act;
c. relatively low level security required for non-sensitive information.

The design traverses these various security levels based on:
d. Deploying the key master as an appliance thus keeping critical processes such as key management, encryption and decryption within a hardened environment rather than running this software on a general purpose computer;
e. Depth of integration with the applications;
f. Optional registered IP address restrictions.

BRIEF DESCRIPTION OF THE DRAWINGS

The accompanying figures, which are incorporated in and constitute a part of the specification, illustrate various example systems, devices methods, and so on, and are used merely to illustrate various example embodiments. It should be noted that various components depicted in the figures may not be drawn to scale, and that the various assemblies and designs depicted in the figures are presented for purposes of illustration only and should not be considered in any way as limiting.

FIG. 2 is a schematic block diagram further illustrating operation of the UHE of FIG. 1.

FIG. 3 is a schematic block diagram illustrating an HCP registration process using the UHE of FIG. 1.

FIG. 4 is a schematic block diagram illustrating a patient registration process using the UHE of FIG. 1.

FIG. 5 is a schematic block diagram illustrating the use of activity logs using the UHE of FIG. 1.

FIG. 6 is a schematic block diagram illustrating sharing write-only data using the UHE of FIG. 1.

FIG. 7 is a schematic block diagram illustrating communications in an emergency situation using the UHE of FIG. 1.

FIG. 8 is a schematic block diagram illustrating mechanisms for identifying fraud, waste and abuse using the UHE of FIG. 1.

FIG. 9 is a schematic block diagram illustrating the generation of de-identified patient data using the UHE of FIG. 1.

FIG. 10 is a schematic block diagram illustrating the key change and/or revocation of access using the UHE of FIG. 1.

FIG. 11 is a schematic block diagram illustrating the key recovery process using the UHE of FIG. 1.

FIG. 12 is a schematic block diagram illustrating the ability to support multiple participant software modules using the UHE of FIG. 1.

FIG. 13 is a schematic block diagram illustrating other alternate environments for the systems, devices, and methods of the present application.

FIG. 15 is a schematic block diagram illustrating other alternate environments for the systems, devices, and methods of the present application.

FIG. 16 is a schematic block diagram illustrating an alternate environment for the systems, devices, and methods of the present application for use in the legal industry.

FIG. 17 is a schematic block diagram illustrating an alternate environment for the systems, devices, and methods of the present application for use in the real estate industry.

FIG. 18 is a schematic block diagram illustrating an alternate environment for the systems, devices, and methods of the present application for use in the real estate industry.

DRAWING REFERENCE NUMERALS

Figure 1:
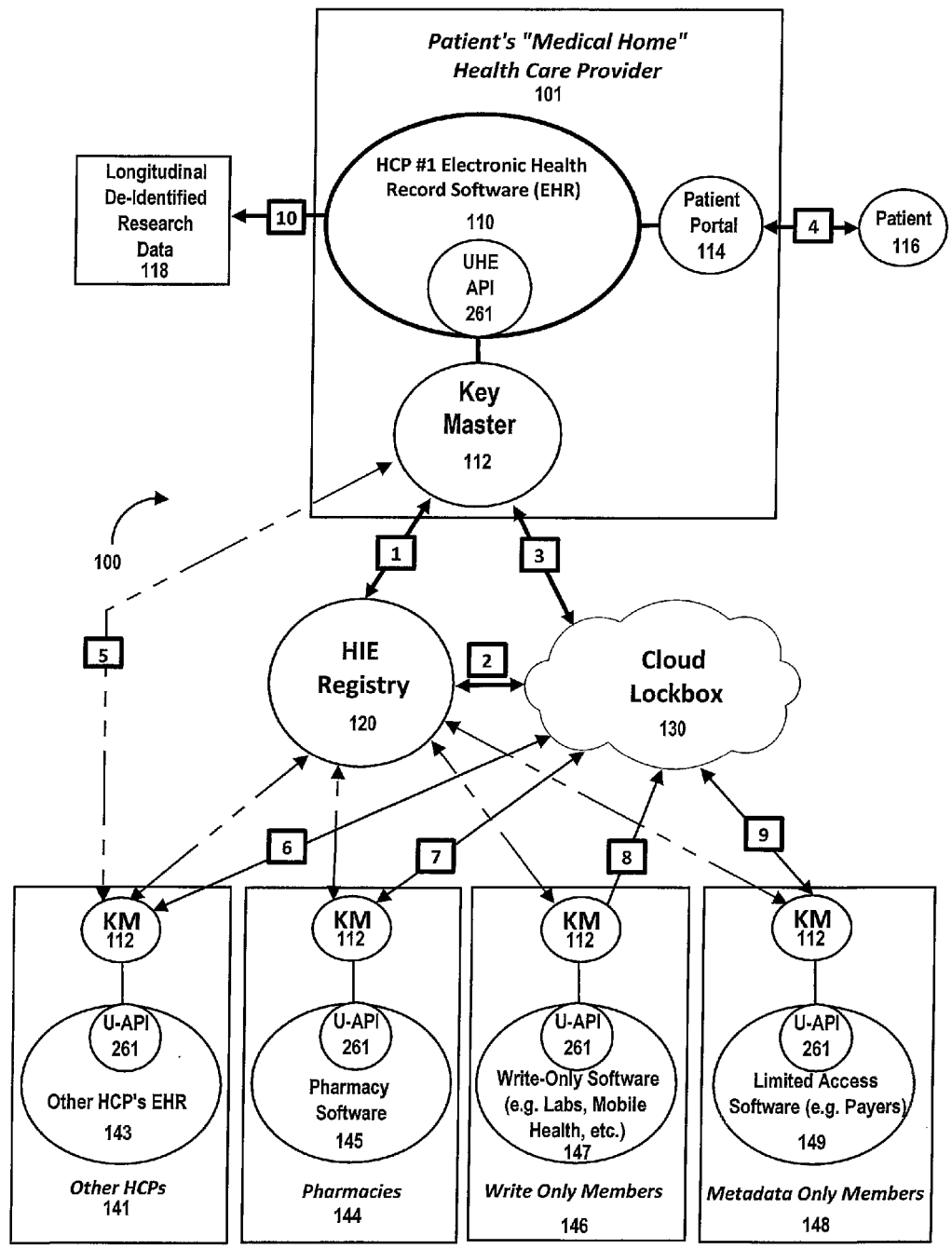
FIG. 1 is a schematic block diagram illustrating an example environment for the systems, devices and methods of the present application.

The following reference characters identify the associated elements depicted in the drawings describing the present invention.

| | |
|---|---|
| 100 | Exemplary environment |
| 101 | Medical Home HCP |
| 110 | HCP #1 Electronic Health Record Software |
| 111 | Activity Log UHE API |
| 112 | Key Master (KM) |
| 114 | Patient Portal |
| 116 | Patient |
| 118 | Longitudinal De-Identified Research Data |
| 120 | HIE Registry |
| 130 | Cloud Lockbox |
| 140 | Secondary HCP |
| 141 | Other HCPs |
| 142 | HCP #2 EHR |
| 143 | Other HCP's EHR |
| 144 | Pharmacies |
| 145 | Pharmacy Software |
| 146 | Write-Only-Members |
| 147 | Write-Only Software (e.g. Labs, Mobile Health, etc.) |
| 146A | Mobile Health Monitor Software |
| 146B | Lab Software |
| 146C | Other Write-Only Software |
| 148 | Metadata-Only Members |
| 149 | Metadata-Only Software (e.g. Payers) |
| 150 | Payer |
| 151 | Payer's Software |
| 152 | HCP #3 EHR |
| 210 | Encrypted EHR Files |
| 210-A | Encrypted HCP #2 Files |
| 211 | File Handler |
| 212 | Permissions Directory |
| 214 | Receptors |
| 216 | Activity Log Cloud Lockbox |
| 250 | Native EHR Files |
| 260 | API Engine |
| 261 | Unified Health Exchange (UHE) Application Programming Interface (UHE-API) (U-API) |
| 262 | Key Manager and File Broker |
| 264 | Activity Log File Broker |
| 281 | HCP Directory |
| 282 | Patient Directory and Permissions |
| 283 | Cloud Lockbox Directory |
| 284 | Registry Directory |
| 310 | Government and Industry DBs |
| 412 | Information Owner Key Master |
| 420-A | HIE Registry - Health Care Community-of-Interest |
| 420-B | Legal Exchange Registry - Legal Community-of-Interest |
| 430-A | Cloud Lockbox for Health Care Community-of-Interest |
| 430-B | Cloud Lockbox for Legal Community-of-Interest |
| 460 | API Engine |
| 461 | Application Programming Interface |
| 462-A | Key Manager and File Broker-A |
| 462-B | Key Manager and File Broker-B |
| 610 | Emergency Room HCP |
| 612 | Emergency Room HCP EHR |
| 910A-910E | HCPs |
| 920A-920C | HIE Registries |
| 1010 | HCP #1 |
| 1011 | HCP #2 |
| 1048 | Write-Only Member(s) |
| 1030A | Cloud Lockbox #1 |
| 1030B | Cloud Lockbox #2 |

DETAILED DESCRIPTION

This present application describes systems, devices, and methods for providing secure exchange of encrypted data using a three-party security mechanism consisting of the key masters operated by the members, the registries, and the cloud lockboxes plus the application programming interfaces.

A member may be an individual directly participating in a community of interest, an organization participating in a community of interest for its own purposes, or an organization participating in a community of interest to represent multiple individuals in which case the individual is participating by proxy.

The members use a key master software (preferably provisioned as an appliance) to:
- Verify the identity and authority of the member in communications with the registry;
- Establish a unique identity and verify authenticity for each individual and organization in communications with the registry;
- Generate individual public-private key pairs for each individual being represented by the member and for the organization itself (if applicable);
- Receive an individual's data and related metadata from the application programming interface;
- Encrypt the data and related metadata with the individual's public key;
- In some uses, encrypt some or all of the metadata with public key of metadata-only recipient;
- Create non-sensitive transactional metadata and append to the files;
- Transmit the encrypted data, metadata, and transactional metadata to cloud lockbox;
- Control of the individual's private key (required for decryption) retained by the member's key master;
- Retrieve files from cloud lockbox and decrypt with an individual's private key;
- With authorization by the individual:
  - Securely transmit an individual's private key to another member's key master to permit decryption of the individual's files;
  - Update permissions lists at registries;
- Transmit activity records of key creation, file retrieval requests, private key exchanges and other activities to the registries;

The registries:
- Establish identity and verify authenticity of members, organizations, other registries and cloud lockboxes;
- Establish unique identities for each individual represented in a community of interest in communications with the key masters, a process which may include communications with additional registries if more than one registry is operational for the community of interest;
- Maintain directories of individuals, members, organizations, and cloud lockboxes and other registries;
- Function as a clearinghouse for members to retrieve public keys of other members, organizations, and cloud lockboxes;
- Manage individual-level access control lists and communicate lists to cloud lockboxes for controlling access to data files;
- Receive activity records from the key masters, the cloud lockboxes, and the application programming interfaces;
  - Analyze activity logs to detect and halt anomalous access;
  - Provide the members with alerts regarding anomalous access and with routine access to activity logs;

The cloud lockboxes:
- Store encrypted data, metadata, and appended transactional metadata;
- Create receptors for stored data to serve as claim tickets for the members;
- Utilize access control lists received from registries to determine which individuals' files a given member may store and retrieve;
- Transmit activity records of file retrieval requests to the registries.

The related application programming interfaces offer flexibility in adapting to the needs of the specific community of interest and/or of the application owner. The application programming interfaces:
- Consist of both publically published and private proprietary methods to integrate to the applications being used by members of a community of interest;
- Support multiple levels of application integration ranging from native integration, in which this mechanism's encryption and protocols are extended into the data stores of the application, to the use of industry-standard interfaces, and to simple archiving solutions and many gradations in between;
- Convert data to/from proprietary to industry standard formats;
- Convert data between key-value data stores to/from relational databases;
- Generate metadata specific to the application that can either be:
  - Appended to the data and encrypted;
  - Encrypted separately from the data so a member could be granted metadata only access;
  - Left unencrypted and added to the transactional metadata created by key master;
- Map individuals' identification numbers in applications to community of interest identification numbers for the same individuals;
- Enable the creation of hybrid cloud and on-premises storage solutions;
- Transmit log records of file retrieval requests, access revocations and other activities to the registries.

Digital signatures verify the identity of members, registries, and cloud lockboxes for all communications and protocols. Encryption protects all sensitive data both in motion and at rest. Optional IP address restrictions add another level to the security model. Appliance-based option for the encryption, decryption and key management further bolsters security.

Any community of interest can establish its own operating parameters including:
- Selecting a public key encryption algorithm;
- Selecting a registry or registries;
- Establishing related membership requirements and identity verification thresholds;
- Selecting a cloud storage provider or providers at which to establish Cloud Lockboxes;
- Selecting from among the optional security measures;
- Determining the minimum application integration levels.

The method also provides protocols and metadata to enable features such as:
- Time-to-live settings to limit the duration of a member's access to the data of an individual's data;
- Key change and file access revocation processes;
- Key and file recovery processes;
- Ability to de-identify the individual's files to facilitate academic or business research.
- Emergency access.

The design supports addition of features by leveraging existing design elements and expanding operating protocols and related metadata.

The method minimizes the exposure of data to system administrators because:

The protected data is encrypted prior to reaching the cloud lockbox;

The cloud lockbox never has the decryption key;

The system administrators performing duties for performance optimization and maintenance of the cloud lockboxes and any applications integrating the mechanism have access to the encrypted data but does not have the decryption keys.

The method can be deployed in various ways to achieve the security level desired by the community of interest ranging from:

The stringent Federal Information Processing Standards 140-2 Level 4;

Rigorous civilian standards for protecting confidentiality such as Health Information Portability and Accountability Act;

The relatively low level security required for non-sensitive information and many levels in between.

The design traverses these various security levels based on:

Deploying the key master as an appliances thus keeping critical processes such as key management, encryption and decryption within a hardened environment rather than running this software on a general purpose computer;

Depth of integration with the applications;

Optional registered IP address restrictions.

The method provides a solution to integrate disparate applications within a single enterprise or across multiple enterprises by converting data in the application programming interfaces to either industry standard representations or proprietary common formats.

The design supports an approach for storing unstructured data in a key-value (object) data stores to simplify sharing and reduces the need for a relational database, yet retains the ability to transfer such information to/from relational databases.

The design supports the ability for the individual to review the contents and audit activity on his/her files.

The design provides the capability to provide a holistic view of the individual's files for individual or authorized member.

The design supports existence of multiple registries and multiple cloud lockboxes.

The design supports use of multiple encryption algorithms simultaneously from a single key master for participation in multiple community-of-interest networks.

The systems, devices, and methods of the present application are well suited to operate in any industry requiring secure storage and exchange of information. The present application will describe an exemplary embodiment in the health care industry. Of course, one of ordinary skill in the art will appreciate that the systems, devices, and methods of the present application will have applicability in other industries, such as the legal service industry and the real estate industry, for example.

Recently, the storage requirements with respect to patient files and the Federal mandates to share records with other health care providers and with patients have presented daunting problems for those in the health care industry. The exemplary systems and methods described herein, generally referred to as a unified health exchange ("UHE"), may be used to solve many of the problems created by the increased storage and usage demands in the industry. The operation of the overall mechanism of the UHE will be described with particular applicability to the health care industry. In the health care application of the design consider the correspondence in the following Table I.

TABLE I

| Generalized | Health Care Specific |
| --- | --- |
| System and Method for Securely Storing and Sharing Information = | Unified Health Exchange |
| Registry = | Health Information Exchange (HIE) Registry |
| Member = | Health Care Provider, Pharmacy, Payer, Patient, etc. |
| Individual = | Patient |
| Individual's Proxy = | Health Care Provider serving as Patient's "Medical Home" |

Problems in the Health Care Industry

The UHE described herein solves critical and previously intractable challenges in the health care industry while simultaneously providing efficient use of resources and generating cost savings. Health care providers ("HCPs") face mounting expenses and downward pressure on reimbursements. Federal mandates require layers of expensive technology that increase the cost of doing business.

Increased Storage Demands

Storage demands for Electronic Health Records ("EHR") continue to expand dramatically, driven by factors including high resolution imaging data, structured and unstructured data, longitudinal care needs and regulatory retention requirements. The combination of increased demand and high cost storage results in rapidly growing IT costs for the HCPs.

Cloud services can dramatically reduce this cost, but cloud providers have been wary of the liability of storing health care records. The Unified Health Exchange solution encrypts records prior to moving them to the cloud lockboxes and the cloud lockboxes and underlying cloud providers never possess the decryption key. This combination eliminates the need for the cloud providers to conduct breach notifications, greatly diminishing their HIPAA exposure.

By relying on the cloud lockboxes for long-term record retention, the HCPs can dramatically reduce the volume and thus the cost for on-premises computer storage. By leveraging intelligent archiving, the HCPs may elect to retain onsite only the records needed in the short term. With deployment of a UHE appliance providing predictive caching, the HCPs could eliminate storage of patient files in their EHRs instead linking the underlying EHR file management to the UHE model. Further, the UHE approach can eliminate duplication of records within a single HCP as well as the duplication of records received from other health care providers.

Financially Sustainable

Existing models for health information exchange involve cumbersome hierarchies of regional, state, and national exchanges that have failed to gain traction. The financial models underpinning most HIEs do not offer a sustainable path, primarily because the current HIEs add incremental costs for HCPs at a time of great budget pressure. Health Care Providers are under increasing deadline pressure to achieve "meaningful use" of health information exchanges.

The Unified Health Exchange design enables HIE by default as a byproduct of the cost-saving storage arrangement with the cloud lockbox combined with the coordination functions of the HIE Registry. Thus the HCP saves money on storage and avoids the cost of supporting a separate HIE infrastructure.

Medical Home

The emerging "medical home" concept offers tremendous promise for coordination of care to improve wellness and reduce costs. The lack of health information exchange continues to hamper implementation of the "medical home" and other innovations such as Accountable Care Organizations (ACOs). Unified Health Exchange consolidates patient records, offering the "medical home" a holistic picture of the patient. A "patient dashboard" may provide an easy overview of the patient's medical history and quick review of recent activity and condition.

Providers and payers struggle to identify fraud, waste, and abuse. The disparate sources of information make compiling a complete view of a patient's care difficult. Once widely adopted, Unified Health Exchange can provide a single source of information for a comprehensive utilization review.

Personal Health Records ("PHR") have been envisioned as a key technology enabling patient education and involvement. Unfortunately, early PHR efforts have failed to:

Win support from health care providers.

Gain the trust of wary consumers over privacy concerns.

The Unified Health Exchange gives patients and/or their "medical home" unprecedented control over their medical records. Because the records are encrypted with individual keys, no one can decrypt the records until authorized for that specific individual.

Computer savvy consumers are able to directly authorize an HCP to access records and also exercise the granularity to only provide permission for specific classes of information. For instance, a podiatrist may not be allowed access to a patient's cardiac records. With Unified Health Exchange, the patient decides who sees what. Further, an audit log of access gives the patient complete visibility regarding who has accessed what and when.

For patients unable or not interested in controlling their own health records, the patient's "medical home" can serve as the patient's proxy by obtaining written sign-off similar to existing HIPAA forms to manage the access on behalf of the client.

The HIPAA and HITECH rules regarding the privacy of health records have created confusion and additional costs across the US health care industry. Unified Health Exchange reduces HIPAA responsibility for cloud lockboxes by encrypting the records. For HCPs, the more of their data they move to UHE, the less vulnerability they retain.

For the EHR vendors, each of the many HIEs utilize unique interfaces to their software. UHE offers a single interface through industry standard methods to connect to what could serve as a global HIE platform.

UHE Operating Environment

Referring now to FIG. 1, there is illustrated an example operating environment 100 of the UHE. Example environment 100 may comprise a medical home HCP 101, an EHR system 110, a patient portal 114, a Key Master 112, an HIE Registry 120, a Cloud Lockbox 130, and various HCPs 141-148. As illustrated, a unified health exchange application programming interface, UHE API 261, and a Key Master 112 may be integrated with medical home's HCP #1 EHR 110 to facilitate communication with HIE Registry 120.

Further, a patient 116 may communicate with Medical Home's EHR 110 via patient portal 114. In addition, the Patient Portal 114 could utilized mobile interfaces to provide convenient interface to the Patient 116 via web or mobile app.

In a typical operation, medical home's HCP #1 EHR 110 using the UHE API 261 and the Key Master 112 assigns a unique public-private key pair and registers patient 116 with HIE Registry 120. The public key is provided to HIE Registry 120, and the private key is retained by medical home 101 in the Key Master 112 as the only entity initially authorized to decrypt patient files. This activity is depicted by reference numeral 1.

The HIE Registry 120 updates permissions directory at Cloud Lockbox 130 to authorize medical home's HCP #1 EHR 110 to write files for patient 114. This activity is depicted by reference numeral 2.

Medical Home's HCP #1 EHR 110 using the UHE API 261 and the Key Master 112 writes patient files encrypted with the public key to the Cloud Lockbox 130, retaining onsite only what is needed in the short term. HCP 110 using the UHE API 261 and the Key Master 112 can retrieve files as needed for longitudinal patient care scenarios. Medical Home HCP 110 using the UHE API 261 and the Key Master 112 can also access, retrieve, and decrypt files written for patient 116 by other participating entities, such as HCPs 141-148. This activity is depicted by reference numeral 3.

Patient 116 authorizes Other HCP 141 to access files as depicted by reference numeral 4. Medical home HCP 110 using the UHE API 261 and the Key Master 112 updates permissions in HIE Registry 120 as depicted by reference numeral 1. HIE Registry 120 updates permissions at Cloud Lockbox 130 in routine synchronization process as depicted by reference numeral 2. Patient 116 can also audit access to his/her files as depicted by reference numeral 4.

Medical home's HCP #1 EHR 110 using the UHE API 261 and the Key Master 112 sends private key of patient 116 directly to Other HCP's EHR 143 using Other HCP's 141 Key Master 112 and the UHE API 261. This exchange of private key is conducted via encrypted transmission verified with digital signatures using the respective organizations public/private key pairs. The key exchange bypasses both the HIE Registry 120 and the Cloud Lockbox 130. This activity is depicted by reference numeral 5.

Other HCP's EHR 143 can now retrieve, decrypt, and read files for the specific patient 116 using the patient's unique public/private key combination. Other HCP's EHR 143 can now also write files for patient 116 to same Cloud Lockbox 130 encrypted using the patient's public key. These activities are depicted by reference numeral 6.

Participation by pharmacies 144, depicted by reference numeral 7, add a useful function for coordination of medication regimens.

Other entities such as labs and patient telemetry providers 146 can write files encrypted with the patient's public key, but cannot retrieve or decrypt files. This reduces HIPAA liability for these entities, and such activities are depicted by reference numeral 8.

Patient-authorized payers 148 are provided limited access to patient files. For example, payers 148 may to review metadata but not detailed file information. This activity is depicted by reference numeral 9.

Further, patient's medical homes HCP #1 EHR 110 may securely contribute records to de-identified research databases 118, as depicted by reference numeral 10.

The exemplary system 100 provides a number of useful features including:

Neither Cloud Lockbox 130 nor HIE Registry 120 ever have decryption keys, reducing HIPAA liability for these entities.

HCPs 101, 141, 144, 146 and 148 save resources through intelligent archiving, enabling them to retain only the files needed in the short term in expensive on-premises storage.

Reductions in record duplication within and between HCP EHRs 110, 143 and related software 145, 147 and 149 also saves resources.

Design supports multiple cloud lockboxes 130 and multiple HIE Registries 120.

Design supports a "glass break" scenario for emergency access to patient files.

Design support key change process, key recovery process, file recovery process, waste/fraud/abuse detection, use of multiple encryption algorithms, and other features.

Unified Health Exchange Components

Referring now to FIG. 2, there is illustrated a schematic block diagram further depicting operation of the UHE of FIG. 1. Each HCP accessing the storage of Cloud Lockbox 130 may comprise or access an HIE Registry 120. In the illustrated example, medical home's HCP #1 EHR 110 utilizes UHE API 261 and Key Master 112 and secondary HCP #2 141 utilizes UHE API 261 and Key Master 112. The HIE Registry 120 provides the mechanisms and trust relationships for verifying unique identities, creating and updating patient-to-HCP and patient-to-cloud lockbox associations, and modifying permissions tables. Each HCP communicates with its associated HIE Registry 120 for patient identity matching to minimize duplication. Each HIE Registry 120 also retains mappings of public keys for patients, HCPs, payers and any other entities involved in UHE. Each HIE Registry 120 also catalogs authorized IP addresses for participating components for all participants.

Although a single Cloud Lockbox 130 is depicted in the example embodiment, it should be clear to those of ordinary skill in the art that multiple cloud lockboxes and/or multiple cloud storage servers may be employed. The cloud lockboxes, such as Cloud Lockbox 130, offer low cost, yet responsive storage for the HCPs Encrypted EHR files 210, which may include file metadata used for the indexing, searching, and features. The cloud lockboxes also retain a Permissions Directory 212 derived from the HIE Registry 120 for determining the mapping of which HCPs can read files for specific patients.

Each of the UHE API 261 comprises software integrated with the HCPs' Electronic Health Record ("EHR") system. The UHE API 261 communicates with the API Engine 260 in the Key Master 112. In turn, the API Engine 260 communicates with the Key Manager and File Broker 262, also a component of the Key Master 112. The API Engine 260 provides a variety of interface options and policy enforcement function. Together these software modules cooperate with the HCP EHRs for issuing and/or managing patient public-private key combinations, interacting with the HIE registries and for reading/writing of files to the cloud lockbox(s). Each Key Master 112 also manages private key exchanges with other HCPs.

The UHE API 261 and the API Engine 260 may also convert proprietary data formats into standards-based formats. Likewise, when reading files from the cloud storage, the key master would convert standardized formats into proprietary formats for local EHR use.

It should be appreciated that the Key Master 112 can be implemented as hardware, software, or a combination of both hardware and software. For example, the Key Master 112 can be implemented, preferably, as a stand-alone appliance that can be inserted and integrated into an existing system architecture. In another example, the Registry & cloud Interface 112 can be implemented or installed onto a computer or other hardware identified and configured by a user. Such a computer may be a dedicated computer, for example, or may share resources between two or more applications or computing processes. A computer may be a suitable computing device having memory and a processor, and capable of storing program instructions in memory and executing the program instructions stored in memory using the processor.

Public Key Encryption and Digital Signatures

In a proxy operation of the design, the patient 116 selects one HCP, HCP 101 in the illustrated embodiment, to serve as his/her "medical home." This medical home HCP #1 EHR 110 using UHE API 261 and Key Master 112 generates a unique pair of encryption keys using a public-private key combination for the patient. The public key is shared with the HCP #1 EHR 110 but the private key is retained only in the Key Manager and File Broker 262 component of the Key Master 112. This activity is depicted by reference numeral 2.

The "public key" would not actually be shared with the general public, but rather it would be shared among HCPs participating in the HIE for file encryption and as a mechanism for identifying the unique patient 116. The public key would also be appended as unencrypted transactional metadata to the files, linking the file to the patient.

The private key, retained by the medical home, would be used to decrypt the data. The Cloud Lockbox would not have the ability to decrypt the files. Only HCPs authorized by the patient would receive the patient's private key, HCPs, cloud lockboxes, and HIE registries also have organization-specific public-private keys utilized for secure communications and digital signatures among registrants.

All communications and updates among entities may be secured through digital signatures and encryption including exchanges between Cloud Lockbox 130 and HIE Registry 120, exchanges between Cloud Lockbox 130 and Key Master 112, between Key Masters 112 of different HCPs, between UHE API 261 and API Engine 260.

IP Address Restrictions

In one example, within a given HCP, communications among components of the UHE and EHRs are restricted to known machine IP addresses to further increase security. Between HCPs, cloud lockboxes, and HIE registries, all communications may also be restricted to known machine IP address to further increase security. In particular, an accepted IP addresses list is maintained by the HIE Registry 120 and distributed along with public keys for these entities. When an individual patient elects to own and operate his/her own Key Master 112 as depicted in FIG. 18, IP restrictions may also be utilized to provide one method to control access.

Unified Health Exchange Operation

The flow of the following permissions and file accesses are depicted in FIGS. 1 and 2:

1. HCP EHR 110, the medical home EHR of patient 116, writes encrypted files to Cloud Lockbox 130 using UHE API 261 and Key Master 112. This includes the UHE API 261 converting the file into a UHE-compatible format and transmitting it to the API Engine 260 in the Key Master 112. The file may include metadata such as, but not limited to, Patient's 116 public key, type of file, and format of file (e.g. what type of reader might be required such as for PACS images). This activity is depicted by reference numeral 2.

2. The API Engine 260 transfers the file within the Key Master 112 to the Key Manager and File Broker 262. The Key Manager and File Broker 262 encrypts the patient's 116 file with patient's public key and transmits it to the Cloud Lockbox 130, thus already protected in motion. The files remain encrypted at rest on cloud server of Cloud Lockbox 130. This activity is depicted by reference numeral 3.

3. The Key Manager and File Broker 262 within the Key Master 112 is the sole location at the Patient's Medical Home 101 where the patient's 116 public-private key pair is retained. Neither Cloud Lockbox 130 nor HIE Registry 120 nor HCP #1 EHR 110 have the patient's private key, thus cannot decrypt files, reducing HIPAA liability. HCP EHR #1 110 has the authority to retrieve and decrypt the Patient's 116 files, but in order to do so must process the request through the Key Master 112 in which the private keys are retained in the Key Manager and File Broker 262. Further, the permission to read and write files for the Patient 116 was initially established in the HCP and Patient registration processes detailed in sections describing FIG. 3 and FIG. 4.

4. Upon receipt of Patient 116 file from HCP #1 110 by Cloud Lockbox 130, File Handler 211 creates a HCP #1 110 specific Receptor 214 for the file. The Receptor 214, encrypted with HCP #1's public key, includes a unique file ID, Patient's 116 public key, time-to-live settings (infinity for creator of file) and other metadata. The file ID is used by the File Handler 211 as a storage location pointer of the file in Encrypted EHR Files 210 store. The file ID will not provide a mapping to Patient 116 identity.

5. Creation by Cloud Lockbox 130 of Receptor 214 and writing of EHR File 210 is recorded in Activity Log 216 at the HIE Registry 120 for review by Patient 116 at will. This activity is depicted by reference numeral 5. FIG. 5 explains the operation of the activity logs in detail.

6. Patient 116 authorizes Medical Home's HCP #1 EHR 110 to release records to Secondary HCP #2 EHR 141. Authorization granted via e-signature using patient portal 114 or via signed paper form. The Patient 116 also has the option of granting access to metadata only. This activity is depicted by reference numeral 1.

7. The Patient 116 also has the option of setting a time-to-live for files retrieved by HCP #2 141. The time-to-live feature limits the period of time that HCP #2 is authorized to retain the Patient's 116 files. The time-to-live setting provides another layer of privacy protection that is included in the hierarchy of levels of integration of UHE into the EHR described later. Patient 116 may be made aware of compliance with time-to-live by HCP #2 141 or by HCP #1 110. Time-to-live settings for entities originating files will be set to infinity to enable use of UHE for archiving and for minimization or eventual elimination of local EHR files.

8. HCP #1 110 using UHE API 261 and Key Master 112 updates HIE Registry 120 with additional access rights of HCP 141 to read specific patient's files. Updates may be secured through digital signature based exchanges between HCP #1 110 and HIE Registry 120. Selections by patient 116 of level of access, i.e. metadata only vs. full file access, time-to-live settings and other variables, also transmitted to HIE Registry 120 by HCP #1 110. This activity is depicted by reference numeral 4.

9. HIE Registry 120 updates Permissions Directory 212 of Cloud Lockbox 130 granting access to Patient's 116 files to HCP #2 141. Selections by patient 116 of level of access, i.e. metadata only vs. full file access, time-to-live settings and other variables, also transmitted to Cloud Lockbox 130 by HIE Registry 120. This activity is depicted by reference numeral 5.

10. Cloud Lockbox 130 using File Handler 211 creates HCP #2 141 specific Receptor 214 for each file of Patient 116 to which HCP #2 has been granted access. The Receptor 214, encrypted with HCP #2's public key, includes a unique file ID, Patient's 116 public key, time-to-live settings and other metadata. The Receptor 214 includes whether the Patient 116 granted the HCP #2 141 full access or metadata only access to the file.

11. HCP #1 110 using UHE API 261 and Key Master 112 sends patient's private key encrypted using public key of HCP #2 141 to HCP #2's Key Master 112. The private key exchange process bypasses Cloud Lockbox 130 and HIE Registry 120, thus only HCPs possess private keys. This activity is depicted by reference numeral 6.

12. The transmission of the Patient's 116 private key is recorded to the Activity Log 111 for review by patient at will. Patient notification triggers would also be supported. This activity is depicted by reference numeral 4.

13. In some situations, the Patient 116 may only want the HCP #2 141 to have access to the metadata. In this case, a variation of the permission process would authorize access to the Receptors 214 but not share the Patient's private key.

14. HCP #2 EHR 141 can now write their own generated content to Cloud Lockbox 130 for the same patient 116. For files written by HCP #2 141, time-to-live settings are set to infinite. This activity is depicted by reference numeral 8.

15. HCP #2 EHR 141 can now retrieve existing patient files written by HCP #1 EHR 110. Using the UHE API 261 and the Key Master 112, HPC #2 EHR transmits a digitally signed request for list of Receptors for Patient 116 identifying individual based on public key of Patient 116. Cloud Lockbox 130 responds with package of Receptors 214 for Patient 116 if authorization for access by HCP #2 141 is already in Permissions Directory 212. This activity is depicted by reference numeral 8.

16. HCP #2 EHR 141, using the UHE API 261 and the Key Master 112, decrypts the Receptors with its own private key. HCP #2 EHR 141 can then decide which files to download based on the Receptor metadata. HCP #2 EHR 140, using the file ID from the Receptor 214, requests the pertinent Encrypted EHR Files 210 for Patient 116. This activity is depicted by reference numeral 8.

17. Access by HCP #2 141 of Patient's 116 Receptors 214 and/or Encrypted EHR Files 210 for files written by any other entity, as well as, for instance, HCP #2 writing files to Cloud Lockbox 130 for Patient, are written to the Activity Log 216 at HIE Registry 120 for review by patient at will. Patient notification triggers would also be supported. This activity is depicted by reference numeral 5.

18. HCP #2 141 using UHE API 261 and Key Master 112 updates HIE Registry 120 with additional access rights of HCP #1 110 to read patient files written by HCP #2 141 for patient 116. This activity is depicted by reference numeral 7.

19. HIE Registry 120 updates permissions directory 212 of Cloud Lockbox 130, adding access for HCP #1 110 to files written by HCP #2 141 for Patient 116. Updates may be secured through digital signature based exchanges between Cloud Lockbox 130 and HIE Registry 120. This activity is depicted by reference numeral 5.

20. Cloud Lockbox 130 using File Handler 211 creates HCP #1 110 specific Receptor 214 for each file for Patient 116 to which HCP #1 has been granted access by HCP #2 EHR 141. The Receptor 214, encrypted with HCP #1's 110 public key, includes a unique file ID, Patient's 116 public key, time-to-live settings and other metadata.

21. HCP #1 EHR 110 also able to retrieve the files generated by HCP #2 EHR 141. This activity is depicted by reference numeral 3.

22. Access by HCP #1 EHR 110 of Patient's 116 Receptors 214 and/or EHR File 210 for files written by any other entity are written to the Activity Log 216 at HIE Registry 120 for review by patient at will. Patient notification triggers would also be supported. This activity is depicted by reference numeral 5.

Encryption Algorithm Flexibility

The UHE environment 100 described herein is designed to protect the privacy and confidentiality of electronic health records and other forms of sensitive information while also allowing such information to be securely shared with others. As such, the UHE environment 100 does not include a central key authority governing the UHE encryption. Rather, each independent Key Master 112 operates a Key Manager and File Broker 462 that generates public-private key pairs and retains the private keys.

Given the modularity and isolation of key creation, encryption, and decryption within the Key Manager and File Broker 462, a given community-of-interest electing to use the UHE mechanism could elect to use any suitable public key encryption algorithm of its choosing without impacting the operation of the UHE environment. For example, a first key master may operate a key master and file broker using a first public key encryption algorithm while a second key master may operate a key master and file broker using a second and different public key encryption algorithm.

In one example, as illustrated in FIG. 18, a Key Master 412 may operate multiple Key Manager and File Broker 462 modules in order to participate in multiple community-of-interest networks utilizing different encryption algorithms.

Details of the HIE Registry

Listed below are examples of the types of information which may be maintained by HIE Registry 120. Of course, the examples listed below are not meant to be exhaustive or prescriptive, but rather merely examples of the ways in which the underlying mechanism may operate.

TABLE B

| HCP Listings |
| --- |
| HCP Listings |
| Name of HCP |
| Type of HCP |
| Public Key of HCP |
| Date Registered |
| Authorization Method |
| Cloud Lockbox |
| IP Addresses |

TABLE C

| HCP Types |
| --- |
| HCP Types |
| Medical Center/Hospital |
| Outpatient Clinic |
| Physician Practice |
| Home Health/Hospice |
| Pharmacy |
| Health Department |
| Lab |
| Mobile/Home Telemetry |

TABLE D

| Patient Listings |
| --- |
| Patient Listings |
| Public Key of Patient |
| Public Key of Medical Home |

TABLE D-continued

| Patient Listings |
| --- |
| Patient Listings |
| Date Registered |
| Authorization Method |
| Public Keys of HCPs Authorized to Read and/or Write Records |
| Key Demographic Information for Identity Matching |
| Payer(s) |

TABLE E

| Directory of Registries |
| --- |
| Directory of Registries |
| HCP-Registry Associations |
| Public Keys of Other Registries |
| IP Addresses |

The activity logs as illustrated in FIG. 5 contain transactional information to monitor access to patient's files. These include the Activity Log UHE API 111, Activity Log File Broker 264 and Activity Log Cloud Lockbox 216. The activity logs provide an essential cross check of file access for security purposes and also provide a rich source of information to inform the patient regarding access to and sharing of the EHR files, private key, etc.

The Cloud Lockbox

Listed below are examples of the types of information that may be stored by the Cloud Lockbox 130. The list is not meant to be exhaustive or prescriptive, but rather an example of one way in which the underlying mechanism may operate.

Encrypted EHR Files 210 may comprise unstructured key-value data store.

Metadata which may be used as key for granular permissions, searching and batch retrievals may include, but is not limited to:
Patient's Public Key
HCP's Public Key
Date of Activity
File Type
Registry Public Key HCPs may write encounter summaries to Cloud Lockbox 130 that include pertinent information such as date(s) of encounter, orders, vital signs, medications, history and physical, radiology report, physicians, discharge summary and links to image files also written to Cloud Lockbox 130. These files may adhere to industry standard formats such as HL7 and be in easily processed formats such as XML.

The Permissions Directory 212 of patients' public keys mapped to HCPs allowed to retrieve information provides an additional level of security to the mechanism beyond the data encryption. All HCP access may be verified via digital signature.

Receptors 214 are created for each file that an HCP is authorized to access. The Receptors 214 are encrypted with the specified HCPs public key. The Receptors include file ID, patient's public key, time-to-live settings, permissions settings, type of file, format of file (e.g. what type of reader might be required such as for PACS images) and other metadata.

File Handler 211 provides the mapping of file ID in the Receptor to the actual storage location of the file at the Cloud Lockbox 130. Thus the physical file location has been obfuscated, requiring the use of the File Handler 211 to retrieve files.

HCP Registration Process

Referring now to FIG. 3, there is a schematic block diagram illustrating an HCP registration process using the UHE of FIG. 1 and FIG. 2. An entity seeking to participate in the UHE network as a HCP Registrant 101-R may be registered as depicted in FIG. 3.

The HIE Registry 120 maintains database of HCPs, labs, telemetry providers, payers and any other entities that may have permission to read and/or write patient files (Registrant). As shown by reference numeral 1, HIE Registry 120 utilizes government sources and other trusted databases to assemble and verify entries in the HIE registry database. HIE Registry 120 may also generate its own public/private key combination for itself as a corporate entity.

As shown by reference numeral 2, a Registrant 101-R may verify its identity and authority with the HIE Registry 120 through multi-factor identity verification and exchange of authorized IP addresses.

Once verification is completed, the Registrant 101-R using HCP #1 EHR 110-R, UHE API 261 and Key Master 112 generates its own public/private key combination to identify itself as a corporate entity.

As shown by reference numeral 3, the Registrant 101-R transmits its public key to HIE Registry 120 encrypted using the HIE registry's public key using the UHE API 261 and the Key Master 112. HIE Registry 120 decrypts with own private key.

As shown by reference numeral 4, HIE Registry 120 replies with an acknowledgement encrypted with its own private key. The Registrant 101-R verifies HIE Registry 120 transmission by decrypting with HIE registry's public key using the UHE API 261 and the Key Master 112.

As shown by reference numeral 5, the Registrant completes registration with an acknowledgement to the HIE Registry 120 encrypted with its own private key using the UHE API 261 and the Key Master 112. HIE Registry 120 verifies the registrant transmission by decrypting with the registrant's public key.

Patient Registration Process

Referring now to FIG. 4, there is a schematic block diagram illustrating a patient registration process using the UHE of FIG. 1 and FIG. 2. Once an entity is registered, as described above, it can then serve as a "Patient's Medical Home" 101 for the patient and conduct the registration process as depicted in FIG. 4.

First, an HCP EHR #1 110 using UHE API 261 and Key Master 112 sends identifying patient demographic information to HIE Registry 120 as shown by reference numeral 1. The payload may be encrypted with the private key of the HCP, decrypted by the HIE Registry 120 with the HCP's public key, confirming the identity of the HCP.

Second, the HIE Registry 120 communicates to its network of HIE Registries if applicable, to verify uniqueness of patient 116 identity as shown by reference numeral 2.

Third, the HIE Registry 120 has three possible replies as shown by reference numeral 3:
  a. EXISTS: In registry, returns patient public key, medical home public key and cloud lockbox.
  b. NEW: Created listing, requests public key of patient.
  c. MORE: Indicating that additional information on patient required to determine whether unique identity.

In all three cases, the response is encrypted with the HIE's private key for decryption by the HCP with the HIE registry's public key, confirming identity of the HIE registry.

Fourth, the HCP replies as shown by reference numeral 4 depending on response in received in step 2:

a. ACKNOWLEDGE: HCP acknowledges receipt and session terminates.
  b. REGISTER: HCP generates public/private key combination for patient. Transmits public key, ID of cloud lockbox and Payer(s) to HIE registry.
  c. Identity confirmation process continues.

In all three cases, the response is encrypted with the HCP's private key for decryption by the HIE registry with the HCP's public key, confirming identity of the HIE registry.

Fifth, the HIE Registry 120 replies as shown by reference numeral 5 depending on response received in step 3:
  a. Session completed in step 3.
  b. HIE registry acknowledges receipt and session terminates.
  c. Identity confirmation process continues.

In all three cases, the response is encrypted with HIE's private key for decryption by the HCP with the HIE registry's public key, confirming identity of the HIE registry.

Sixth, if the Patient 116 is a new patient to the HIE Registry network, then the HIE Registry 120 updates Cloud Lockbox 130 regarding registration of new Patient 116 as shown by reference numeral 6.

Seventh, the Patient's Medical Home 101 is now able to write and read files to the Cloud Lockbox 130 for Patient 116 using the HCP #1 EHR 110, the UHE API 261 and the Key Master 112.

Activity Logs Mechanism for Patient Information and for Detecting and Halting Unauthorized Access Referring now to FIG. 5, a schematic block diagram illustrates creating and comparing Activity Logs using the UHE of FIG. 2. Creation and comparison of Activity Logs are also supported by the example UHE environment.

An Activity Log UHE API 111, an Activity Log File Broker 264 and an Activity Log Cloud Lockbox 216 capture information representative of writing and reading of UHE files as well as information representative of changes to access by different members. For improved security, the Activity Logs are maintained at the HIE Registry 120 separate from the sources of Activity Log records. For example, Activity Logs may be maintained in a first data store while UHE files may be maintained in a second distinct data store. An Activity Logs Compare module 280 at the HIE Registry 120 provides a method for detecting and halting unauthorized access to files. The Activity Logs also provide a record of actions for review by the Patient 116.

Activity Log data may be obtained from one or more of a variety of sources. For example, when the UHE API 261 that is integrated with HCP #1 EHR 110 sends a file write or read request to the API Engine 260 in the Key Master 112 as depicted by reference numeral 1, the UHE API 261 simultaneously sends a report of the request to the Activity Log UHE API 111 at the HIE Registry 120 as depicted by reference numeral 2.

In one example, when the Key Manager and File Broker 262 in the Key Master 112 sends a file write or read request to the Cloud Lockbox 130 as depicted by reference numeral 3, the Key Manager and File Broker 262 simultaneously sends a report of the request to the Activity Log File Broker 264 at the HIE Registry 120 depicted by reference numeral 4.

In one example, when the File Handler 211 in the Cloud Lockbox 130 responds to a file write or read request depicted by reference numeral 3, the File Handler 211 simultaneously sends a report of the request to the Activity Log Cloud Lockbox 216 at the HIE Registry 120 depicted by reference numeral 5.

Periodically, the HIE Registry 120 will analyze activity logs, using Activity Log Compare module 280, to detect anomalies that could indicate unauthorized access to Encrypted EHR Files 210 stored at the Cloud Lockbox 130 depicted by reference numeral 6. If such an anomaly is detected, then the HIE Registry 120 may alter the Permissions Directory 212 of the Cloud Lockbox 130 in order to halt file retrieval from the suspect Key Master 112 depicted by reference numeral 7. In one example, a Permission Directory 212 setting may indicate to the Key Manager and File Broker 262 the reason for the denial of file retrieval depicted by reference numeral 3. In one example, the HIE Registry 120 may also notify responsible members at the Participating HCP about the detected anomaly and denial of file retrieval. The notification may be performed via a suitable method established at the time of registration depicted by reference numeral 8. For example, a notification may include an email message, a text message, a telephone call, a pager alert, and so on.

Even in a proxy situation, the patient 116 could also receive notification of the anomalous access and the actions taken to halt such access.

In one example, the File Handler 211, Key Manager and File Broker 262, and the UHE API 261 may send periodic "heartbeat" messages to HIE Registry 120 to confirm ability to communicate. In such an example, the Activity Log Compare module 280 is able to detect the absence of heartbeat entries and generate a notification accordingly.

Inclusion of Write-only-members

Referring now to FIG. 6, there is a schematic block diagram illustrating sharing write-only data using the UHE of FIG. 1 and FIG. 2. Receiving and sharing lab results and home/mobile telemetry is also supported by the example UHE environment.

Certain providers in the health care field provide patient data without being allowed to receive patient data. Such providers, generally referred to generally as Write-Only Members, may include participating vendors providing home or Mobile Health Monitor Software 146A, participating labs running Lab Software 146B and other participating entities with Write-Only Software 146C.

Like other HCPs, these Write-Only-Members may also associate to and register with an HIE Registry 120 in the UHE network by following the entity registration process described above in reference to FIG. 3.

By following a process similar to patient registration described in reference to FIG. 4, the write-only Mobile Health Monitor Software 146A, using the UPI API 261 and the Key Master 112, may retrieve a patient's public key and the ID of Cloud Lockbox 130 from the HIE Registry 120 as depicted by reference numeral 1. The Write-Only Participant 146A could then commence writing files encrypted with patient's public key to Cloud Lockbox 130 as depicted by reference numeral 1.

Only HCPs authorized by the patient would have the private key to decrypt the files written by Write-Only-Members. Write-Only-Members 146A, 146B and 146C would not possess any patients' private keys nor would such participants be authorized to retrieve files from the Cloud Lockbox 130.

"Glass Break" Emergency Care Scenario

Referring now to FIG. 7, there is a schematic block diagram illustrating communications within the UHE environment in an emergency situation.

It is important for an HIE solution to provide emergency rooms with access to patient data in the event of an emergency that occurs outside of the patient's normal care community. The so-called "glass break" scenario outlined in the FIG. 7, shows how such functionality may work within the UHE framework.

1. Patient 116 presents to an emergency room 610, unable to provide authorization for access to his/her medical records depicted by reference numeral 1. The emergency room 610 is not one of the patient's normal HCPs.
2. Emergency room 610 using ER HCP EHR 612, UHE API 261 and Key Master 112 attempts to register patient 116 with HIE Registry 120 and, as a result, receives patient's medical home 101 public key and Cloud Lockbox 130 depicted by reference numeral 2.
3. Emergency room 610 sends request to HCP #1 EHR 110 for emergency-based release of private key using UHE API 261 and Key Master 112. Message to HCP 110 is encrypted with emergency room's private key. HCP 110 is able to decrypt message with emergency room's public key, verifying identity. Encrypted key exchange proceeds. These activities are depicted by reference numeral 3.
4. HCP 110 using UHE API 261 and Key Master 112 updates permission directory 220 at HIE Registry 120 allowing access to Patient's 116 EHR files 210 stored at Cloud Lockbox 130 for ER HCP EHR 612 depicted by reference numeral 4.
5. HIE Registry 120 updates permissions directory 212 at Cloud Lockbox 130 This activity is depicted by reference numeral 5.
6. Emergency room 610 using ER HCP EHR 612, UHE API 261 and Key Master 112 can now retrieve and decrypt patient files from Cloud Lockbox 130. Emergency room 610 also writes encounter summary and other files generated during encounter to the Cloud Lockbox 130 for later review by HCP 110. This activity is depicted by reference numeral 6.

If Emergency room 610 has not yet joined an applicable community of interest, then a similar mechanism would support emergency access to the records through the use of existing methods for sharing records such as the Direct Project or Blue Button.

Detecting and Preventing Waste, Fraud and Abuse

In addition to the coordination of care and HIE benefits of UHE, the mechanisms also support analytical methods to detect and prevent waste, fraud and abuse as illustrated in FIG. 8.

1. HCP 101, medical home of patient 116, using HCP #1 EHR 110, UHE API 261 and Key Master 112, generates a summary digest of all files written to Cloud Lockbox 130 and of all other HCP reads of files for its patients. Such a summary supports coordination of care, and triggers alerts to duplicated prescriptions, and redundant tests, among other things. Further, HCP EHR #1 110 provides data for patient review of activity on his/her health records. These activities are depicted by reference numeral 1.
2. Payer 150 also registers with HIE Registry 120 in a process similar to registration of HCPs depicted by reference numerals 2 and 3.
3. Payer 150, identified by HIE Registry 120 as Payer for the Patient 116, is able to review metadata for patients' files stored by Cloud Lockbox 130 by using UHE API 261 integrated with the Payer's Software 151 and Key Master 112. Payer 150 is not able to decrypt the contents without further authorization and related private key exchange. Thus payer 150 can identify some utilization trends with minimized HIPAA exposure. These activities are depicted by reference numeral 4.
4. Payer 150 and Patient's Medical Home 101 may collaborate to identify cases of waste, fraud and abuse depicted by reference numeral 5.

5. Insurance form submittals may also be written to Cloud Lockbox 130 by HCP #1 EHR 110, encrypted with the payer's public key, providing a simple mechanism for securely submitting and cataloging the reimbursement paperwork. The same document may also be written to the Cloud Lockbox 130 encrypted with the patient's public key. These activities are depicted by reference numeral 1.
6. Payer 150 using Payer's Software 151, UHE API 261 and Key Master 112 may retrieve reimbursement paperwork and write updates to such paperwork for review by Patient's Medical Home 101 as depicted by reference numeral 5.
7. Patient 116 is able to review all access to their files via patient portal 114 depicted by reference numeral 6.

Support for Medical Research

Using the UHE environment 100 described herein, one or more HCPs may elect to generate coordinated and longitudinal de-identified patient care research databases 118. Permission to extract such information may be solicited at the time the patient 116 is authenticated at his/her medical home 101. The coordinated care benefits would ripple into the research database, providing a complete picture of the individual's health history without any personal identifiers remaining. The communication mechanisms that support the generation of de-identified patient data is illustrated in FIG. 9.

- Patient's medical home 101 using the HPC #1 EHR 110, UHE API 261 and Key Master 112 provides a full view of the medical status and activities of patient 116.
- Files may be written to a de-identified patient database 118 with a "scramble" of the patient's 116 private key to replace the public key as a patient identifier with this new number.
- The relationship of the new "scrambled" identifier to the actual patient public key may be known only to the Patient's medical home 101.
- Patient's Medical Home 101 may retain the mapping so that additional data for the patient can be added over time for longitudinal studies.

Key Chance and Access Revocation

Circumstances may arise in which the need for a change of the Patient's 116 public-private key pair is required. This need could arise from circumstances such as: compromise of the privacy of the public-private key pair; detection of unauthorized access to EHR files 210 at Cloud Lockbox 130; decisions to revoke decryption authority previously granted to one or more HCPs; or decision of Patient 116 to switch to a different HCP as its medical home. Regardless of the reason the mechanism to change or revoke access remains the same and is illustrated in FIG. 10.

Upon receiving a request to change or revoke access, HCP #1 EHR 110 using UHE API 261 and Key Master 112 generates a new key pair and updates HIE Registry 120 with the change via a digitally signed transaction including both the old and new public keys of Patient 116 depicted by reference numeral 1.

HIE Registry 120 updates Permissions Directory 212 with the change and with an indication that key change process is about to commence for Patient 116 via digitally signed transaction depicted by reference numeral 2.

Permissions Directory 212 and File Handler 211, both at Cloud Lockbox 130, prepare a new set of Receptors for Patient's 116 files.

Patient's Medical Home 101, using HCP #1 110, UHE API 261 and Key Master 112, then transmits the digitally signed request for the current and new list of Receptors 214 for Patient 116. HCP #1 EHR 142 identifies Patient 116 based on both the old and new public keys of Patient 116. Cloud Lockbox 130 responds with two packages of Receptors 214 for the Patient 116, both the old and the new, each encrypted with HCP #1's 110 public key. These activities are depicted by reference numeral 3.

HCP #1 110 using Key Master 112 retrieves all Encrypted EHR Files 210 for Patient 116, decrypts the files with the Patient's 116 old private key and re-encrypts the files with the Patient's 116 new public key. HCP #1 EHR 110, using UHE API 261 and Key Master 112, then writes Encrypted EHR Files 210 for Patient 116 back to Cloud Storage 130 as managed by the File Handler 211. These activities depicted by reference numeral 3.

HCP #1 EHR 110, using the UHE API 261 and Key Master 112, erases the old version of the Patient's 116 Encrypted EHR Files 210. However, the files written to Cloud Storage 130 by HCP #2 EHR 142, now designated at 210-A, the entity whose access is being revoked, are not erased. This measure is necessary so that HCP #2's internal operations are not compromised in terms of retaining patient files. These activities depicted by reference numeral 3.

Cloud Lockbox 130 records the activity in the Activity Log Cloud 216 maintained at HIE Registry 120 as depicted by reference numeral 2.

HCP #1 EHR 110, using UHE API 261 and Key Master 112, notifies other HCPs still authorized to write to Patient's files such as HCP #3 EHR 152 of the Patient's new public key depicted by reference numeral 4. HCP #1 EHR 110, using Key Master 112, also notifies other HCPs still authorized to read and decrypt Patient's files such as HCP #3 EHR 152 of the Patient's 116 new private key depicted by reference numeral 4.

HCP #1 EHR 110, using UHE API 261 and Key Master 112, also issues a file revocation request to the Key Master 112 of HCP #2 EHR 142 for all files that HCP #2 142 has downloaded for Patient 116 other than those file written by HCP #2 EHR 142 depicted by reference numeral 5.

If HCP #2 EHR 142 software is compliant with this feature of UHE, then it can acknowledge using Key Master 112 the destruction of Patient's 116 Encrypted EHR Files 210 that it had downloaded but not created as depicted by reference numeral 5.

HCP #1 EHR 110, using UHE API 261 and Key Master 112, writes to Activity Log R&CI 216 maintained at the HIE Registry 120 the outcome of revocation requests and the notification of HCPs still authorized to write and/or read files depicted by reference numeral 1.

It should be appreciated that, although the file revocation process has been described as occurring in combination with a key change request, a file revocation request can also occur independently of a key change process.

In one example, HCP #2 142, using UHE API and Key Master 112, can continue to retrieve and decrypt the files it wrote to Patient's 116 record using the old private key now shown as HCP #2 Encrypted EHR Files 210-A. This measure allows HCP #2 EHR 142 to continue to use the Cloud Lockbox 130 for archival purposes of its own activity. However, HCP #2 EHR 142 will no longer be able to retrieve or learn of the existence of other Encrypted EHR Files 210 for the Patient 116. These activities depicted by reference numeral 6.

Key Recovery and/or File Recovery

The UHE environment 100 described herein is designed to protect the privacy and confidentiality of electronic health records and other forms of sensitive information while also allowing such information to be securely shared with others. As such, there is no central key authority governing the UHE design. Each Key Master 112 operates a Key Manager and File Broker 262 that generates public-private key pairs and retains the private keys. Thus a complete loss of the private key(s) would render the information protected inaccessible without massive computational effort to recover the private key. Only files remaining in local EHR storage would be recoverable directly from within UHE.

This aspect of potential loss of private keys of UHE is a privacy-enhancing design feature but does call out the importance of sharing the private keys with at least one other member with its Key Master 112 operating at sufficient physical distance to provide for disaster recovery scenarios. Alternatively, HCP #1 EHR 110 may install and register a second Key Master 112 that is automatically granted read and write access for any Patient 116 selecting HCP #1 as its Medical Home 101.

In the event that a Key Master 112 becomes damaged, corrupted or otherwise loses private keys under its control, the key recovery process would in most cases resolve the loss of private keys as illustrated in FIG. 11.

In the worst case scenario, the Patient's Medical Home 101 has suffered a corruption of the Key Master 112 such that the private key of one or more patients has been lost. Thus, the entire operation of the Key Master 112 may have failed.

First the Patient's Medical Home 101 rectifies operational problem affecting the Key Master 112 and re-establishes registration of the new software instance with the HIE Registry 120 as depicted by reference numeral 1.

The U-API 261 initiates through the Key Master 112 the key recovery process using the public key of affected patients.

The Key Master 112 then initiates the key recovery process with the HIE Registry 120. HIE Registry replies with a private key holder, e.g. HCP #2 EHR, for one or more patients based on the Patient Directory and Permissions 282. These activities are depicted by reference numeral 1.

The HIE Registry 120 sends to the Key Master 112 of HCP #2 EHR 142 a list of patients for whom HCP #1 EHR 110 needs private key recovery as depicted by reference numeral 2. Alternatively, if Patient's Medical Home 101 had installed and registered a second Key Master 112, the HIE Registry 120 initiates the key recovery process with this backup Key Master 112 first. The remainder of the process would remain as follows.

Key Master 112 of HCP #2 EHR 142 transmits private keys for patients in a list from HIE Registry 120 to the Key Master 112 of HCP #1 EHR 110 as depicted by reference numeral 3. This communication would be further secured by digital signatures and optionally IP address restrictions.

Key Masters 112 HCP EHR #2 142 records this activity in the Activity Log File Broker 264 as depicted by reference numeral 2.

The HIE Registry 120 then sends to the Key Masters 112 HCP #3 EHR 152 a list of patients for whom the Key Masters 112 of HCP #1 EHR 110 needs private key recovery as depicted by reference numeral 4.

Key Master 112 of HCP #3 EHR 152 transmits private keys for patients in a list from HIE Registry 120 to the Key Master 112 of HCP #1 EHR 110 as depicted by reference numeral 5. This communication would be further secured by digital signatures and optionally IP address restrictions.

Key Masters 112 HCP EHR #3 152 records this activity in the Activity Log File Broker 264 as depicted by reference numeral 4.

The described process repeats until Patient's Medical Home retrieves private keys for all affected patients.

Should the key for a patient 116 be unrecoverable, the Patient's Medical Home 101 may initiate a file recovery process that seeks to restore to the UHE network whatever EHR files for the Patient 116 remain in local storage of the HCP EHR participating in the care of the given Patient 116. The key change process from FIG. 10 and a modification of the key recovery process from FIG. 11 that focuses on files instead of keys are then invoked.

Multiple UHE APIs at a Participating HCP

A Participating HCP will in most cases operate multiple EHR software systems as well as other auxiliary systems requiring data feeds from EHR systems. These software systems are likely to include but not be limited to an inpatient EHR, I-EHR 110-A; an ambulatory EHR, A-EHR 110-B; and a picture archiving and communication system, PACS 110-C as illustrated in FIG. 12. These various systems often function independently within a health care organization, requiring internal integration to create a unified view of a given patient.

Each of the EHR software systems will need to run an interface to participate in UHE called the UHE API 261. However only a single Key Master 112 would be required, with the API Engine 260 able to communication with multiple UHE APIs 261.

In such a configuration, UHE can support internal HCP integration efforts by providing the common interface among all systems. For vendors of EHR systems, UHE presents a single interface to develop that would serve HCPs with any blend of EHR systems.

Multiple HIE Registries

While it would be simpler to have a single HIE registry to serve all patients, this outcome seems unlikely in our highly competitive health care and IT markets. One of ordinary skill in the art will recognize that the UHE described herein may be embodied in alternate configurations, including an environment having multiple HIE registries as illustrated by FIG. 13.

In such an embodiment, each HCP 910A-910E associates with only one HIE registry 920A-920C. The HIE registries 920A-920C communicate with each other during:

Patient registration process to confirm uniqueness.
Exchange of HCP registrations.
Exchange of patient record permissions changes, e.g. new HCP authorized by patient.

Multiple Cloud Lockboxes

While it would be simpler to have a single provider of cloud lockboxes to serve all HCPs, one of ordinary skill in the art will recognize that such a configuration may not accommodate the highly competitive health care and IT markets. Thus, the UHE design accommodates the existence of multiple providers of cloud lockboxes as illustrated in FIGS. 14A and 14B.

Figures 14A, 14B:
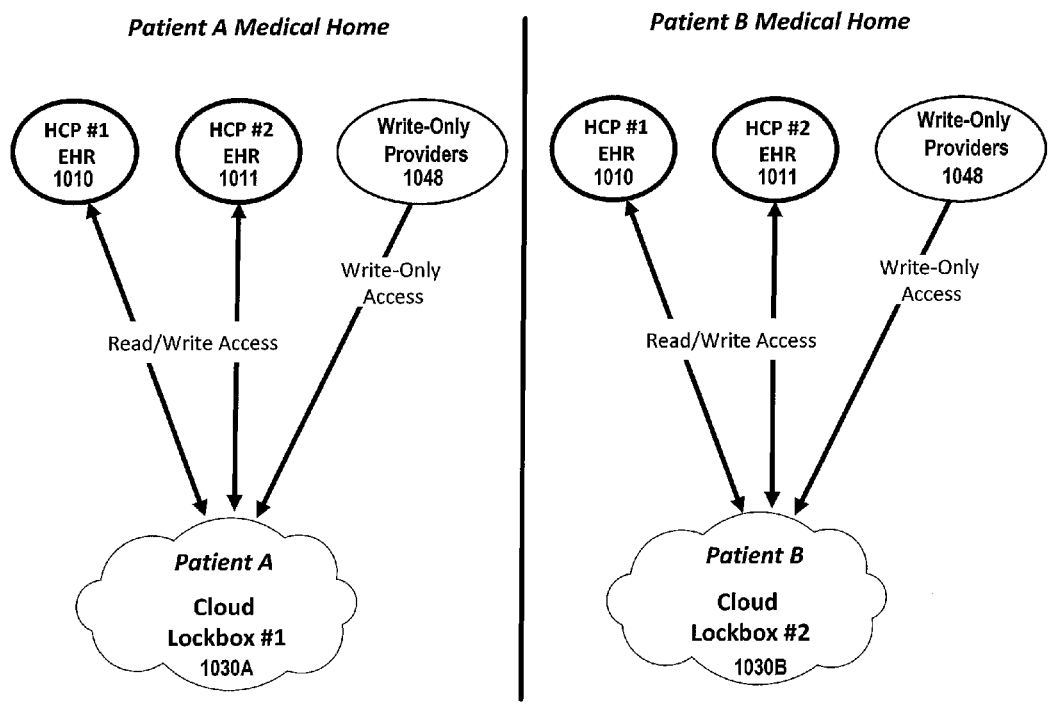
FIGS. 14A and 14B are a schematic block diagrams illustrating other alternate environments for the systems, devices, and methods of the present application.

As illustrated in FIG. 14A, HCP 1010 is the medical home for patient A. HCP 1010 designates cloud lockbox 1030A for patient A. The association is identified during HIE registration of the patient. Patient A authorizes HCP 1011 to read/write files. HCP 1011 writes files for patient A to cloud lockbox 1030A to keep all patient files in one source. Similarly, write-only input for patient A, such as lab results from HCP 1048, are also written to cloud lockbox 1030A.

As illustrated in FIG. 14B, HCP 1011 is the medical home for patient B. HCP 1011 designates cloud lockbox 1030B for patient B. The association is identified during HIE registration of the patient. Patient B authorizes HCP 1010 to read/write files. HCP 1010 writes files for patient B to cloud lockbox 1030B to keep all patient files in one source. Similarly, write-only input for patient B, such as lab results from HCP 1048, are also written to cloud lockbox 1030B.

Levels of Integration

It should be appreciated different levels of integration may be possible between EHRs and the UHE. For example, evolution and extension of the interfaces will progress over time.

All levels of integration may be supported by a single API Engine 260 in the Key Master 112. An example delineation of the levels of integration is depicted in the following table.

TABLE 2

Levels of EHR Integration with UHE

| | |
|---|---|
| Level 1 | Method for backing up or archiving EHR files. |
| Level 2 | Engaged in a network of providers for health information exchange. |
| Level 3 | Honor incoming revocation requests. Honor time-to-live settings in meta data. |
| Level 4 | Retain full metadata in native EHR file storage. Provide identity of individual who accesses patient files for additional detail in activity logs. |
| Level 5 | Use of UHE with local caching as primary file store. |

Data Access Options

In some situations, it may not be necessary to access complete data records but rather to only access a partial record of a patient, such as basic patient information. For example, an insurer may need to know that a certain diagnostic test was performed but the insurer does not need to have access to a full patient file. In another example, a physician specializing in one field, such as podiatrist, may not need to have access to patient information pertaining to another medical field, such as the patient's records about a patient's heart condition. Thus, in one example, a partial data record such as metadata may be provided rather than the entire patient data file.

In some situations, it may be undesirable to provide data from which specific patient identities can be determined. For example, an organization performing research may be interested in patient outcomes in relation to a specific treatment of a disease. However, the organization performing the research may not be permitted to know the identities of the patients. Thus, in one example, patient data may be anonymized in order to eliminate information such as names, addresses, and social security numbers.

Patient Dashboard

In one example, the patient portal 114 may further provide patient 116 with a patient dashboard. In particular, the patient dashboard may provide an overview of the patient's 116 medical history as well as an overview of recent activity and medical conditions. Such a patient dashboard provides a single source of information from which a patient 116 may obtain a personal medical summary as well as a comprehensive medical review.

Alternative Business Models in Health Care

Given the flexibility of the described systems, devices and methods, the UHE business model could take other forms. FIG. 15 illustrates one such alternate embodiment. FIG. 15 depicts an environment similar to that of FIG. 1 except that an entity other than a health care provider may become a patient's medical home for the purposes of medical record aggregation, called a "Medical Home" Health Record Representative ("HRR").

The HCPs are or will soon be required by Federal mandate to be able to share patient records through a set of HIE standards. Thus, the HIE goals of UHE could be met even if the HCP did not directly participate in the UHE mechanism. Such an HCP would sacrifice the cost savings inherent in the UHE design in terms of reducing storage costs unless they transferred their long-term record retention responsibilities to the HRR.

The HRR could also operate a blended architecture offering a choice between the standards-based HIE-interface solutions and the full UHE implementation.

Other Industries

The systems, devices and methods of the present application have been described primarily in relation to an example health care system. The systems, devices and method are also applicable in a wide variety of other industries in which confidential information needs to be selectively and securely shared among multiple business entities.

Legal Industry

Referring now to FIG. 16, there is illustrated a schematic block diagram depicting a system supporting the legal industry, using a similar design as in FIG. 1 for the medical industry, but with different entities. Following the concept of the "medical home" this model addresses the creation of a "legal home" for the client. Such a "home" selection does not preclude the use of other lawyers, but the "home" lawyer does become the initial issuer and owner of the public/private key set. Similar to the health care industry, other business entities could provide the "legal home" other than law firms.

Other law firms, prosecutors and courts may be granted granular read-write access on a client-by-client basis. Write-only participants such as court reporters and labs could securely write files to the client's case file without gaining the ability to retrieve and/or decrypt any other files related to the case. The client would have a complete view of all files related to his/her case and the ability to audit access.

Real Estate Industry

Referring now to FIG. 17, there is illustrated a schematic block diagram depicting a system supporting the real estate industry, using a similar design as in FIG. 1 for the medical industry, but with different entities. Once again following the concept of the "medical home" this model addresses the creation of a "real estate home" for the client. Such a "home" selection does not preclude the use of other realtors, but the "home" realtor does become the initial issuer and owner of the public/private key set. Similar to the health care industry, other business entities may provide the "real estate home" other than real estate firms.

Other realtors, mortgage brokers, lawyers, developers, etc. may be granted granular read-write access on a client-by-client basis. Write-only participants such as appraisers and inspectors could securely write files to the client's file without gaining the ability to retrieve and/or decrypt any other files related to the business situation. The client may have a complete view of all files related to his/her business situation and the ability to audit access.

Information Owner Controlled

The preceding depictions of the system have assumed the presence of a proxy acting on the information owners request to manage the owner's information. However, as shown in FIG. 18, an example design also supports a stand-alone use of the mechanism operated by the owner to directly manage multiple types of information using a similar design as in FIG. 1. In this scenario there is no "medical home" or "legal home" with default access. Instead, the information owner originates the key-pairs and all permissions. In this scenario, all activities including registration, sharing of private keys, revocation requests and key pair changes would originate with the owner using his/her own Key Master 412.

The API Engine 460 could support APIs 461 for a variety of desktop and mobile applications running on any suitable operating system.

In one example, information owner may elect to run multiple Key Manager and File Broker modules 462 in the Key Master 412. In this way, the Information Owner can participate in multiple community-of-interest networks operating with different encryption algorithms. In this example, the Key Master 412 contains two Key Manager and File Brokers, 462-A and 462-B each operating a different encryption algorithm specific to the two specific communities-of-interest depicted. In particular, Key Manager and File Broker-A 462-A uses an encryption algorithm shared by all members of the community-of-interest participating in the health care network represented by Cloud Lockbox Health Care 430-A and HIE Registry 420-A. Key Manager and File Broker-B 462-B uses an encryption algorithm shared by all members of the community-of-interest participating in the legal network represented by Cloud Lockbox Legal 430-B and Legal Exchange Registry 420-B. Thus, a single Key Master 412 could support multiple Key Manager and File Broker 462 modules for participation in multiple community-of-interest networks.

Wide Applicability

With three examples of industries that can utilize the described systems, devices and methods, one can easily imagine other applications of this flexible system in any situation in which multiple members need to have access to confidential information regarding an individual, such as the insurance industry, social service agencies, commercial research and development, scientific research, and finance, for example.

From the information contained herein, those skilled in the art will perceive improvements, changes and modifications to the systems, devices and methods disclosed herein. Such improvements, changes, and modifications within the skill of the art are intended to be covered by the present application.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, devices, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the devices, systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A system having a plurality participant devices for conducting a secure exchange of encrypted data within a community of interest using a three-party security mechanism consisting of:
    a cloud lockbox configured to:
        receive and store encrypted data submitted by at least one of the plurality participant devices;
        create a receptor providing transactional metadata and a file identification; and
        acknowledge the receipt of the encrypted data by communicating the receptor;
    a key master operated in a participant device of the plurality of participant devices of the community of interest, the key master configured to:
        generate a public-private key pair for each participant device of the plurality of participant devices in the community of interest;
        receive a participant device's data and related metadata;
        encrypt the received data and related metadata with the participant device's public key;
        create non-sensitive transactional metadata and associate the non-sensitive transactional metadata with the participant device's data and related metadata;
        transmit the encrypted data, metadata, and transactional metadata to the cloud lockbox; and
        maintain the participant device's private key required for decryption of the encrypted data; and
        retrieve the encrypted data and encrypted metadata by submitting the receptor to the cloud lockbox;
    a registry, remotely coupled to the cloud lockbox and the key master, configured to:
        establish unique identities for each participant device of the community of interest with the key master, wherein the registry is configured to communicate with additional registries if more than one registry is operational for the community of interest;
        establish a unique identity and authenticity of the cloud lockbox;
        maintain a directory of participants and the cloud lockbox, wherein the registry is configured to function as a clearinghouse for participant devices to retrieve public keys of other participant devices; and
        manage a participant-level access control list and communicate the list to the cloud lockbox for controlling access to stored data by the key master;
        record an IP address for each of the key master, the cloud lockbox and the registry for selectively restricting communications;
    wherein the key master and the registry are configured to update permissions for the plurality of participant devices to enable the plurality of participant devices to add or retrieve data based on the participant-level access control list; and
    wherein the three-party security mechanism is configured to be integrated with via an application programming interface.

2. The system of claim 1, wherein a customized community of interest is generated based on a selection of at least one of a plurality of options among built-in operating parameters, comprising:
    a. selecting a public key encryption algorithm;
    b. selecting a registry or a plurality of registries;

c. establishing membership requirements and identity verification thresholds;
d. selecting a cloud storage provider at which to establish the cloud lockboxes;
e. selecting from among a plurality of optional security measures;
f. determining a minimum application integration level; and
g. determining initial metadata structure, purpose, and meaning.

3. The system of claim 1, wherein the three-party security mechanism is vendor-neutral, thereby enabling underlying software to security-enable any records management, file sharing, document management or similar application software.

4. The system of claim 1, wherein the three-party security mechanism as a standalone service.

5. The system of claim 1, wherein the plurality of participant devices are associated with participant devices of the community of interest, the participant of the community of interest comprising at least one of:
a. an individual participating directly;
b. an organization participating for its own purposes; and
c. an organization participating to represent multiple individuals, whereby the multiple individuals are participating by proxy.

6. The system of claim 5, wherein the three-party security mechanism provides the multiple individuals participating by proxy the ability to access data; to review activity logs; and to receive alerts regarding anomalous access.

7. The system of claim 1, wherein a key master is configured to:
a. verify identities, authenticity, and authority of the participant device in communication with the registry;
b. establish a unique identity and verify authenticity for each participant device in communications with the registry;
k. securely transmit the participant device's private key to another participant device's key master to permit decryption of the data received from the participant device;
l. update permissions lists at the plurality of registries;
m. transmit log records of key creation, file retrieval requests, private key exchanges, and other activities to the registry.

8. The system of claim 1, wherein the three-party security mechanism is configured to use unencrypted transaction metadata as indexing elements, to provide information representative of transactional information as defined by the community of interest, including information about data source and date of storage.

9. The system of claim 1, wherein a registry is configured to:
g. receive activity logs from the key master, the application program interface, and the cloud lockbox to:
i. analyze activity logs to detect and halt anomalous access; and
ii. provide alerts regarding anomalous access and with routine access to activity logs; and
h. conduct polling at random intervals of the key master, the application programming interface, the cloud lockbox, and other registries to verify accessibility of activity reporting module.

10. The system of claim 1, wherein a cloud lockbox comprises software operating at a cloud provider, the cloud lockbox being configured to:
a. store encrypted data, encrypted metadata, and unencrypted metadata;
b. create receptors for stored data to serve as claim tickets for the members; wherein the receptor obfuscates the physical location of the file in the cloud lockbox;
c. utilize access control lists received from the registries to determine which individuals' files a given member may store and retrieve;
d. enable push notifications to members of new receptor availability; and
e. transmit activity records of file retrieval requests to the registries.

11. The system of claim 1, wherein an application programming interface is configured to:
d. convert data between a plurality of formats;
e. convert data between a key-value data store and a relational database;
f. generate metadata specific to the application, wherein the metadata is one of:
i. appended to data and encrypted with the data;
ii. encrypted separately from the data; and
iii. left unencrypted and added to the transactional metadata created by the key master by:
1. using unencrypted metadata as indexing elements, information about the source of the data; and
2. using unencrypted metadata to enable granular access control;
g. map the participant device's identification numbers in applications to community of interest identification numbers for the same participant device;
h. enable the creation of a hybrid cloud and an on-premise storage solution; and
i. transmit activity records of file retrieval requests and access revocations to the registries.

12. The system of claim 1, wherein the three-party security mechanism is configured to enable:
a. changing keys;
b. revoking access;
c. recovering keys;
d. recovering files;
e. de-identifying files; and
f. providing emergency access.

13. The system of claim 1, wherein the three-party security mechanism is configured to offer a plurality of security levels by:
a. deploying the key master as an appliance;
b. integrating applications with the mechanism to provide additional information, including an internal application username of a person requesting data;
c. requiring two-factor authentication for access to the key master; and
d. applying IP address communications restrictions based on information gathered by the registry.

14. The system of claim 1:
a. wherein the registry is configured to communicate to the cloud lockbox permissions of the key master for the participant device to store data in the cloud lockbox for the participant device;
b. wherein the registry is configured to communicate to the cloud lockbox the public key of the participant device and the key master;
c. wherein the registry is configured to selectively communicate to the cloud lockbox the IP address of the key master;
d. wherein the key master is configured to encrypt the data and metadata with first the participant device's public key;

e. wherein the key master is configured to encrypt at least a portion of the metadata with a metadata-only participant device's public key.

15. The system of claim 1, wherein the three-party security mechanism is configured to enable sharing encrypted data between participant devices:
   a. wherein the registry is configured to receive data indicative of a first participant device's request to share encrypted data received from the first participant's device and stored on the cloud lockbox with a second participant device, wherein the first participant device previously verified its identity with the registry;
   b. wherein the registry is configured to update permissions for the second participant device specific to the first participant device using the key master of the first participant device;
   c. wherein the registry is configured to update the cloud lockbox with permissions for the second participant device for specified data received from the first participant device as authorized by the first participant device;
   d. wherein the key master of the first participant device is configured to transmit a private key of the first participant device, to a key master of the second participant device, encrypted with the second participant device's public key;
   e. wherein the key master of the second participant device is configured to decrypt and store the participant device's private key; and
   f. wherein the key master of the second participant device is configured to retrieve and decrypt data received from the first participant device, from the cloud lockbox.

16. The system of claim 1, wherein the three-party security mechanism is configured to enable reciprocal sharing of encrypted data:
   a. wherein a key master of a second participant device is configured to originate data about an individual associated with a first participant device and encrypt the data and metadata with the public encryption key of the first participant, and add the encrypted data and metadata to the cloud lockbox; and
   b. wherein the key master of the first participant device is configured to retrieve and decrypt the data originated by the second participant device for the individual associated with the first participant device.

17. The system of claim 1, wherein a key master is configured to verify identities of other key masters, registries and cloud lockboxes during transactions using digital signatures.

18. The system of claim 1, wherein the three-party security mechanism is configured to enable write-only access:
   a. wherein the key master of the participant device is configured to update permissions for a write-only participant device requiring write-only access to enable the write-only participant device to add files to the cloud lockbox for a individual associated with the participant device;
   b. wherein the registry is configured to update the cloud lockbox with permissions for the write-only participant device, to store data for, but not retrieve data for, the individual associated with the participant device;
   c. wherein a key master of the write-only participant device is configured to encrypt data with the public key of the participant device and add the data to the cloud lockbox of the participant device;
   d. wherein the key master of the participant device is configured to retrieve and decrypt the data originated by the write-only participant device for the individual associated with the participant device.

19. The system of claim 1, wherein the three-party security mechanism is configured to enable metadata-only access:
   a. wherein the key master of the participant device is configured to update the registry with permissions for a metadata-only participant device to retrieve metadata only for an individual associated with the participant device;
   b. wherein the registry is configured to update the cloud lockbox with permissions for the metadata-only participant device to retrieve only metadata of the individual associated with the participant device.

20. The system of claim 1, wherein the three-party security mechanism is configured to enable detecting and halting anomalous access:
   a. wherein the registry is configured to collect activity records from the key master, the application programming interface, and the cloud lockbox for actions associated with, data, keys or metadata and generate activity logs;
   b. wherein the registry is configured to analyze the activity logs to detect anomalous access to data;
   c. wherein the registry is configured to communicate with the cloud lockbox to halt access to the affected data responsive to detecting anomalous access to data; and
   d. wherein the registry is configured to notify the the participant device of anomalous access and halting of access.

21. The system of claim 1, wherein the three-party security mechanism is configured to enable a time-to-live feature:
   a. wherein the application programming interface in combination with the key master of the participating device is configured to enable the participating device to create metadata including a time-to-live value for the data in accordance with an agreement within the community of interest; and
   b. wherein the key master in combination with the application programming interface is configured to enable the participating device to retrieve data with time-to-live metadata and to acknowledging one of ability and lack of ability to honor the time-to-live setting.

22. The system of claim 1, wherein the three-party security mechanism is configured to enable changing a key pair:
   a. wherein the key master of the participating device is configured to generate a new public-private key pair for the participant device responsive to receiving a request to change the participant device's public-private key pair;
   b. wherein the key master is configured to notify the registry of the new public key for the participant device;
   c. wherein the registry is configured to notify the cloud lockbox of a key change for the participant device;
   d. wherein the cloud lockbox is configured to facilitate the retrieval of all of the affected data;
   e. wherein the key master is configured to decrypt the data with an old private key and re-encrypt the data with the new public key;
   f. wherein the key master is configured to transmit the re-encrypted files to the cloud lockbox;
   g. wherein the cloud lockbox is configured to acknowledge receipt of re-encrypted files and to provide new receptors to the key master; and
   h. wherein the key master of the participant device is configured to transmit the new private key to a key master of a participant device.

23. The system for claim 1, wherein the three-party security mechanism is configured to enable recovery of a private key:

a. wherein the key master of a-first participant device is configured to recover the first participant device's private key from a key master of a second participating device with access to the private key, the process being mediated by the registry.

24. The system of claim 1, wherein the community of interest spans a plurality of cloud providers for provisioning cloud lockboxes.

25. The system of claim 1, wherein the community of interest spans multiple registries, wherein the multiple registries are configured to communicate among one-another in the community of interest to maintain unique identities.

26. The system of claim 1, wherein the community of interest comprises one of:
   a. a small group of individuals;
   b. all individuals residing in a given country; and
   c. a number of individuals connected through any type of affiliation.

27. The system for claim 1, wherein the key master is configured to participate in a plurality of communities of interest, wherein each of the plurality of communities of interest:
   a. requires a different encryption algorithm;
   b. requires a different identity verification process; and
   c. utilizes different cloud lockboxes.

28. The system for claim 1, wherein the three-party security mechanism is configured to minimize exposure of data to system administrators:
   a. wherein data stored in a cloud lockbox is encrypted;
   b. wherein the cloud lockbox does not have the decryption key; and
   c. wherein a system administrator is provided with access to encrypted data but is not provided with access to the decryption key.

29. The system of claim 1, wherein the three-party security mechanism is configured to enable emergency access to the data:
   a. wherein the three-party security mechanism is configured to enable access, to encrypted data received from a first participant device, by an emergency participating device in the event of an emergency in which the first participant device cannot provide authorization;
   b. wherein the three-party security mechanism is configured to require an emergency participant device to at least one of have previously registered as a member of the community of interest and have a previously registered participant device act on its behalf;
   c. wherein the three-party security mechanism is configured to provide the emergency participating device a private key of the participant device responsive to receiving a request for emergency access; and
   d. wherein the three-party security mechanism is configured to log all activity for review.

30. The system of claim 1, wherein the three-party security mechanism is configured to create a holistic view of the participant device participating in the community of interest by generating summaries, comparisons and alerts regarding the participant device, given access to data from all participants for the participant device.

31. The system of claim 1, wherein the three-party security mechanism is configured to enable a hybrid cloud and on-premise storage solution with the key master offering predictive caching and the application programming interface deeply integrated into an application.

32. The system of 1, wherein the three-party security mechanism is configured to enable application integration across one of a single enterprise and multiple enterprises by converting disparate data models to a common data model with sharing of data occurring across the mechanism.

* * * * *